(12) United States Patent
Evans et al.

US008685432B2

(10) Patent No.: US 8,685,432 B2
(45) Date of Patent: Apr. 1, 2014

(54) CONTROLLED RELEASE TISSUE GRAFT COMBINATION BIOMATERIALS

(75) Inventors: Bruce G. Evans, Sandy, UT (US); David Christopher Evans, Sandy, UT (US); Paul C. Hogrebe, Salt Lake City, UT (US); David W. Grainger, Salt Lake City, UT (US); Amanda Elaine Brooks, Highland, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 377 days.

(21) Appl. No.: 12/409,261

(22) Filed: Mar. 23, 2009

(65) Prior Publication Data

US 2009/0324683 A1 Dec. 31, 2009

Related U.S. Application Data

(60) Provisional application No. 61/070,638, filed on Mar. 25, 2008.

(51) Int. Cl.
*A61F 2/28* (2006.01)
*A61F 2/30* (2006.01)
*A61K 6/00* (2006.01)

(52) U.S. Cl.
USPC .......................................... 424/426; 427/2.26

(58) Field of Classification Search
None
See application file for complete search history.

(56) References Cited

U.S. PATENT DOCUMENTS

| | | | |
|---|---|---|---|
| 5,164,187 A | 11/1992 | Constantz et al. | |
| 5,475,063 A | 12/1995 | Kaplan et al. | 525/411 |
| 5,522,895 A | 6/1996 | Mikos | 623/16 |
| 5,679,723 A | 10/1997 | Cooper et al. | 523/115 |
| 5,766,618 A | 6/1998 | Laurencin et al. | 424/426 |
| 6,165,486 A * | 12/2000 | Marra et al. | 424/423 |
| 6,224,794 B1 | 5/2001 | Amsden et al. | |
| 6,284,758 B1 | 9/2001 | Egi et al. | |
| 6,368,346 B1 | 4/2002 | Jadhav | 623/1.22 |
| 6,586,246 B1 | 7/2003 | Yoon et al. | 435/396 |
| 6,716,450 B1 | 4/2004 | Yin et al. | |
| 6,846,853 B2 | 1/2005 | Shimp | |
| 6,869,445 B1 | 3/2005 | Johnson | 623/17.11 |
| 6,893,465 B2 | 5/2005 | Huang | 623/17.12 |
| 6,949,251 B2 | 9/2005 | Dalal et al. | 424/423 |
| 6,991,647 B2 | 1/2006 | Jadhav | 623/1.2 |
| 7,012,106 B2 | 3/2006 | Yuan et al. | 523/115 |
| 7,022,522 B2 | 4/2006 | Guan et al. | 435/395 |
| 7,041,641 B2 * | 5/2006 | Rueger et al. | 424/486 |
| 7,122,057 B2 | 10/2006 | Beam et al. | 623/23.51 |
| 7,230,039 B2 | 6/2007 | Trieu et al. | 523/113 |
| 7,270,813 B2 | 9/2007 | Shimp et al. | 424/93.7 |
| 7,291,345 B2 | 11/2007 | Winterbottom et al. | 424/400 |
| 7,357,941 B2 | 4/2008 | Dalal et al. | 424/423 |
| 7,371,400 B2 | 5/2008 | Borenstein et al. | 424/423 |
| 7,390,498 B2 | 6/2008 | Dalal et al. | 424/423 |
| 7,572,298 B2 | 8/2009 | Roller et al. | 623/23.75 |
| 7,759,113 B2 | 7/2010 | Vacanti et al. | 435/284.1 |
| 7,776,021 B2 | 8/2010 | Borenstein et al. | 604/406 |
| 7,815,826 B2 | 10/2010 | Serdy et al. | 264/49 |
| 7,815,926 B2 | 10/2010 | Syring et al. | 424/423 |
| 7,837,740 B2 | 11/2010 | Semler et al. | 623/23.63 |
| 7,842,737 B2 | 11/2010 | Wang et al. | 523/113 |
| RE42,208 E | 3/2011 | Truncale et al. | 424/93.7 |
| 7,901,457 B2 | 3/2011 | Truncale et al. | 623/16.11 |
| 7,959,940 B2 | 6/2011 | Gale et al. | 424/423 |
| 7,989,532 B2 | 8/2011 | Li et al. | 524/417 |
| 8,012,210 B2 | 9/2011 | Lin et al. | 623/17.12 |
| 8,016,865 B2 | 9/2011 | Donnelly et al. | 606/301 |
| RE43,116 E | 1/2012 | Johnson | 623/17.11 |
| 8,119,705 B2 | 2/2012 | Wang et al. | 523/113 |
| RE43,258 E | 3/2012 | Truncale et al. | 424/548 |
| 8,167,787 B2 | 5/2012 | Gillis | 600/37 |
| 8,167,955 B2 | 5/2012 | Marrs et al. | 623/23.72 |
| 8,173,149 B2 | 5/2012 | Dalal et al. | 424/423 |
| 8,173,361 B2 | 5/2012 | Vacanti et al. | 435/4 |
| 8,178,013 B2 | 5/2012 | Kim | 264/40.5 |
| 8,192,665 B2 | 6/2012 | Huang et al. | 264/211.13 |
| 8,221,500 B2 | 7/2012 | Truncale et al. | 623/16.11 |
| 8,282,912 B2 | 10/2012 | Molenberg et al. | 424/78.08 |
| 8,292,968 B2 | 10/2012 | Truncale et al. | 623/23.51 |
| 8,293,530 B2 | 10/2012 | Burgess et al. | 435/372 |
| 8,309,114 B2 | 11/2012 | Gale et al. | 424/423 |
| 8,327,854 B2 | 12/2012 | Gillis et al. | 128/848 |

(Continued)

FOREIGN PATENT DOCUMENTS

| | | |
|---|---|---|
| EP | 0 243 178 | 10/1987 |
| EP | 1 390 086 | 12/2004 |

(Continued)

OTHER PUBLICATIONS

Boyce, T. et al. "The influence of processing on safety and performance." *Orthop Clin North Am* 30(4):571-81 (1999).
Chen, C. et al. "Results of vancomycin-impregnated cancellous bone grafting for infected tibial nonunion." *Arch Orthop Trauma Surg* 125(6):369-75 (2005).
Davidoff, S. et al. "A Robust Method to coat allograf bone with a drug-releasing polymer shell." BioMed 2010.
Fonge, H. et al. "Bioanalysis of tobramycin for therapeutic drug monitoring by solid-phase extraction and capillary zone electrophoresis." *J. Chromatography B*. 810:313-318 (2004).

(Continued)

*Primary Examiner* — Robert A Wax
*Assistant Examiner* — H. Sarah Park
(74) *Attorney, Agent, or Firm* — Sunstein Kann Murphy & Timbers LLP

(57) ABSTRACT

In one aspect, the invention relates to tissue graft combination biomaterials capable of controlled release of bioactive agents or pharmaceutically active agents through a rate-controlling polymer coating encapsulating the graft material, methods for preparing same, methods of controlled release using same, and methods for treating tissue defects. This abstract is intended as a scanning tool for purposes of searching in the particular art and is not intended to be limiting of the present invention.

7 Claims, 9 Drawing Sheets

(56) References Cited

U.S. PATENT DOCUMENTS

| | | | |
|---|---|---|---|
| 8,357,528 B2 | 1/2013 | Vacanti et al. | 435/284.1 |
| 8,377,356 B2 | 2/2013 | Huang et al. | 264/209.1 |
| 2004/0064193 A1* | 4/2004 | Evans et al. | 623/23.51 |
| 2005/0249697 A1 | 11/2005 | Uhrich et al. | |
| 2007/0240725 A1 | 10/2007 | McKay | |
| 2008/0124400 A1 | 5/2008 | Liggins et al. | |
| 2008/0139987 A1 | 6/2008 | Ambrosio et al. | 602/43 |
| 2009/0048358 A1 | 2/2009 | Kim | |
| 2009/0130173 A1 | 5/2009 | Behnam et al. | 424/426 |
| 2009/0248172 A1 | 10/2009 | Neuenschwander | 623/23.75 |
| 2009/0287300 A1 | 11/2009 | Dave et al. | 623/1.42 |
| 2009/0324683 A1 | 12/2009 | Evans et al. | 424/426 |
| 2010/0021545 A1 | 1/2010 | Chaput et al. | 424/488 |
| 2012/0029653 A1 | 2/2012 | Evans et al. | 623/23.72 |

FOREIGN PATENT DOCUMENTS

| | | |
|---|---|---|
| WO | WO 2002/087649 | 11/2002 |
| WO | WO 2008/149096 | 12/2008 |
| WO | WO 2011/127149 A1 | 10/2011 |

OTHER PUBLICATIONS

Frommelt, L. "Principles of systemic antimicrobial therapy in foreign material associated infection in bone tissue, with special focus on periprosthetic infection." *Injury* 37 Suppl 2, pp. S87-S94 (2006).

Gubernator, J. et al. "A simply and sensitive flurometric method for determination of gentamicin in liposomal suspensions." *Internat'l J. of Pharm.* 327:104-109 (2006).

Kokubo, T. et al. "Solutions able to reproduce in vivo surface-structure changes in bioactive glass-ceramic A-W." *J. Biomed. Mater. Res.* 24:721-734 (1990).

Lochmann, D. et al. "New protamine quantification method in microtiter plates using o-phthaldialdehyde/N-acetyl-L-cysteine reagent." *Internat'l J. of Pharm.* 283_11-17 (2004).

Mashat, M. et al. "Development and validation of HPLC method for the determination of tobramycin in urine samples post-inhalation using pre-column derivatisation with fluorescein isothiocyanate." *J. Chromatog B.* 869:59-66 (2008).

Pedersen, E. et al. "Plasma amino acids in Greenlanders and Danes. Influence of Seasons, Residence, Ethnicity, and Diet." *Am. J. Human Biol.* 18:99-111 (2006).

Rhyu, K. et al. "In vitro release of vancomycin from vancomycin-loaded blood coated demineralised bone." *Int Orthop* 27(1):53-5 (2003).

Sayin, B. et al. "Implantation of vancomycin microspheres in blend with human/rabbit bone grafts to infected bone defects." *J. Microencapsul* 23(5):553-66 (2006).

Sevy, J. et al. "Assay Method for polymer-controlled antibiotic release from allograft bone to target orthopaedic infections." Paper—BioMed 2010.

Stadelmann, V. et al. "Implants delivering bisphosphonate locally increase periprosthetic bone density in an osteoporotic sheep model." *Eur Cell Mater.* 16:10-16 (2008).

Trampuz, A. et al. "Diagnosis and treatment of infections associated with fracture-fixation devices." *Injury* 37 Suppl 2, pp. S59-S66 (2006).

Walenkamp, G. wt al. Gentamicin-PMMA beads. Pharmacokinetic and nephrotoxicological study. *Clin Orthop Relat Res* 205:171-83 (1986).

Winkler, H. et al. "In vitro release of vancomycin and tobramycin from impregnated human and bovine bone grafts." *J. Antimicrob. Chemotherapy* 46:423-428 (2000).

Witso, E. et al. "Cortical allograft as a vehicle for antibiotic delivery." *Acta Orthop* 76(4):481-6 (2005).

Witso, E. et al. "Release of netilmicin and vancomycin from cancellous bone." *Acta Orthop Scand* 73(2):199-205 (2002).

Witso, E. et al. "Cancellous bone as an antibiotic carrier." *Acta Orthop Scand* 71(1):80-4 (2000).

Witso. E. et al. "Adsorption and release of antibiotics from morselized cancellous bone. In vitro studies of 8 antibiotics." *Acta Orthop Scand* 70(3):298-304 (1999).

Wu et al. "Drug/device combinations for local drug therapies and infection prophylaxis." *Biomaterials* 27:2450-2467 (2006).

Lee W. Young, *Authorized officer* ISA/US, Commisioner for Patents, International Search Report—International Application No. PCT/US2011/031394, dated May 23, 2011 (2 pages).

Shane Thomas, *Authorized officer* International Searching Authority, International Search Report—Application No. PCT/US2013/024792, mailed on Apr. 16, 2013, *along with Written Opinion of the International Searching Authority* (8 pages).

U.S. Appl. No. 13/645,918, filed Oct. 5, 2012, Controlled Release Combination Biomaterials, Brooks et al.

U.S. Appl. No. 13/759,904, filed Feb. 5, 2013, Drug Release from A Polymer-Controlled Local Antibiotic Delivery System Using A Degradable Bone Graft, Brooks et al.

* cited by examiner

CONTROLLED RELEASE TISSUE GRAFT COMBINATION BIOMATERIALS

CROSS-REFERENCE TO RELATED APPLICATIONS

This application claims benefit of U.S. Provisional Application No. 61/070,638, filed Mar. 25, 2008, which is hereby incorporated herein by reference in its entirety.

BACKGROUND

Currently, there are many types of bone fillers and grafting biomaterials on the market approved for human implant use. Commercial examples include tricalcium phosphate, calcium sulfate, hydroxyapatite, and processed cadaveric allograft human bone grafts in large pieces, croutons and morsels, particles and powder forms intended for implant and surgical use. These products provide surrogate structural support in bone defect and musculoskeletal implant sites, and act as osteoconductive agents, or biomaterial scaffolds, to facilitate bone tissue regeneration, mechanical restoration of function, healing and structural re-integration of existing tissues. A second category of bone regenerative materials are called osteoinductive agents, usually in the form of small bioactive molecules and human purified recombinant growth factors (proteins) or extracted natural protein mixtures that stimulate or induce endogenous bone formation. Examples include Bone Morphogenetic Proteins (BMPs), statins, bioactive peptides (e.g., P15), and Demineralized Bone Matrix (DBM). These osteoinductive agents can be combined with osteoconductive biomaterials carriers in attempts to provide both benefits to patients.

Current clinically approved bone filler materials are problematic in patients because they are associated with several clinical problems, including lack of effective healing and tissue regeneration, lack of vascularity, insufficient structural and mechanical properties, and a high potential for developing infections at the surgical, trauma or implant site. Consequently, where bone loss is associated with an active infection or chronic lack of healing, currently available bone fillers are not recommended. The potential risk of introducing bone graft materials into an active infection, also at implant sites, requires a two-stage surgical procedure in which the infection is first eradicated, often requiring implant retrieval and resultant trauma, followed by implant replacement and subsequent bone grafting with autologous, synthetic, or allogenic graft materials.

Active infection at implant sites in and around bones and joints, in musculoskeletal trauma sites with or without implants, and in reducing open and closed fractures with and without fixation tooling, all remain problematic due to the prolonged systemic and/or local antibiotic treatments required for reliable resolution. Currently, when an infection is present, antibiotic is delivered to implant and trauma sites and bone defects through systemic drug infusions, through locally placed but temporary bone cement carriers, and direct topical use, all of which intend to deliver sufficient antibiotic dosing to the wound site. Antibiotic bone cement carriers placed locally into wound sites (e.g., cement beads containing antibiotics) allow the antibiotics to leach from the cement over a period of weeks. Much of the loaded drug dose is unable to leach from these solid, glassy matrices over extended times due to the dense delivery matrix and lack of ready drug transport within these carriers. Additionally, typical non-degrading or thermosetting cement-loaded matrices intended to resolve wound and implant infections require two surgical operations: one for placing the cement-drug matrix into the wound site, and a second for removal of the cement after drug dose exhaustion. Presently, no commercially available permanently implanted bone fillers or synthetic or allografted bone substitutes are able to incorporate an integrated drug, growth factor, antibiotic or combination agent release scheme.

Current techniques of delivering drugs, growth factors, and antibiotics locally into an active implant or bone infection site include the simple topical application of drug solutions, use of a drug-soaked collagen membrane or sponge, and use of polymer bone cement loaded with antibiotic drugs, usually as a soluble drug solution or solid drug powder dispersion, directly to the wound site. Numerous studies examining the drug leaching or elution properties of bone cement have demonstrated that the greatest concentration of drug release occurs within the first 8-10 days (so-called burst effect) followed by a reduced dose, with tapering release often too low to produce reliable therapy. Intravenous antibiotics are delivered to patients with bone and implant infections for an average of 6 to 8 weeks. Therefore, it is beneficial to have a local source of antibiotic release at these sites above the microbial killing threshold (e.g., minimal inhibitory concentration) and within the infection site for a similar time of 6 weeks, to reliably clear such infections from the implant and surrounding tissue sources of re-seeded infection.

Another problem that occurs in both orthopedic and dental surgery, as well as trauma and implant placement, is the occurrence of infection when bone grafting is used to fill bone defects. Typically, the rate of infection is greater when a bone graft is used than when it is not used, and with implants compared to no implants. Bone graft substitutes do not have or rapidly encourage an active host blood supply and cannot be adequately perfused by host defense components (cells and antibodies) and serum-circulating antibiotics. This "dead tissue" surrogate, while acting as a filler in the wound or defect site, can also serve as a perfect site for colonization, allowing infection to occur and persist.

Thus, needed are bone graft substitutes and fillers with antimicrobial properties that can incorporate and release multiple drug types in programmed ways to wound and surgical sites: antimicrobial agents alone or in tandem with osteoinductive agents or other pharmacologically active substances to produce effective tissue generation with osteoinducing agents plus microcidal antibiotic concentrations at the local site for extended time periods (6-8 weeks), affecting both opportunistic pathogens known to colonize wound and implant sites, those already present, and those that persist despite systemic therapy.

SUMMARY

Disclosed are tissue graft combination biomaterials comprising a biocompatible, osteoconductive, porous substrate; a degradable polymer coated on the substrate surface; and one or more bioactive agents or pharmaceutically active agents encapsulated by polymer, wherein the polymer has a structure and a molecular weight selected to biodegrade over a time period when implanted within a subject and thereby release the agent over the time period.

Also disclosed are methods for preparing a tissue graft combination biomaterials comprising the steps of providing a biocompatible, osteoconductive, porous substrate; combining an effective amount of a bioactive agent or pharmaceutically active agent with the substrate; and coating the substrate surface with a degradable polymer.

Also disclosed are the products of the disclosed methods.

Also disclosed are methods for introducing a tissue graft combination biomaterial, the method comprising the steps of providing a tissue graft combination biomaterial comprising a biocompatible, osteoconductive, porous substrate; a degradable polymer coated on the substrate surface; and a bioactive agent or pharmaceutically active agent encapsulated by the polymer, wherein the polymer has a structure and a molecular weight selected to biodegrade over a time period when implanted within a subject and thereby release the agent over the time period; introducing the composite into a subject.

Also disclosed are methods for treating a tissue defect, comprising the steps of identifying a subject having a tissue defect in need of treatment; providing a tissue graft combination biomaterial comprising a biocompatible, osteoconductive, porous substrate; a degradable (e.g., biodegradable, resobrable) polymer coated on the substrate surface; and a bioactive agent or pharmaceutically active agent encapsulated by the polymer, wherein the polymer has a structure and a molecular weight selected to biodegrade over a time period when implanted within a subject and thereby release the agent over the time period; and introducing the composite into a subject proximate to the tissue defect.

Also disclosed are uses of a tissue graft combination biomaterial for treating a subject having a tissue defect, the combination biomaterial comprising a biocompatible, osteoconductive, porous substrate; a degradable (e.g., biodegradable, resobrable) polymer coated on the substrate surface; and a bioactive agent or pharmaceutically active agent encapsulated by the polymer, wherein the polymer has a structure and a molecular weight selected to biodegrade over a time period when implanted within a subject and thereby release the agent over the time period.

Also disclosed are kits comprising at least two combination biomaterials or products of disclosed methods, wherein the at least two combination biomaterials comprise different bioactive or pharmaceutically active agents.

Also disclosed are kits comprising at least two disclosed combination biomaterials or products of disclosed methods and instructions for introducing the combination biomaterials into a subject.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several embodiments and together with the description serve to explain the principles of the invention.

Figure 1:
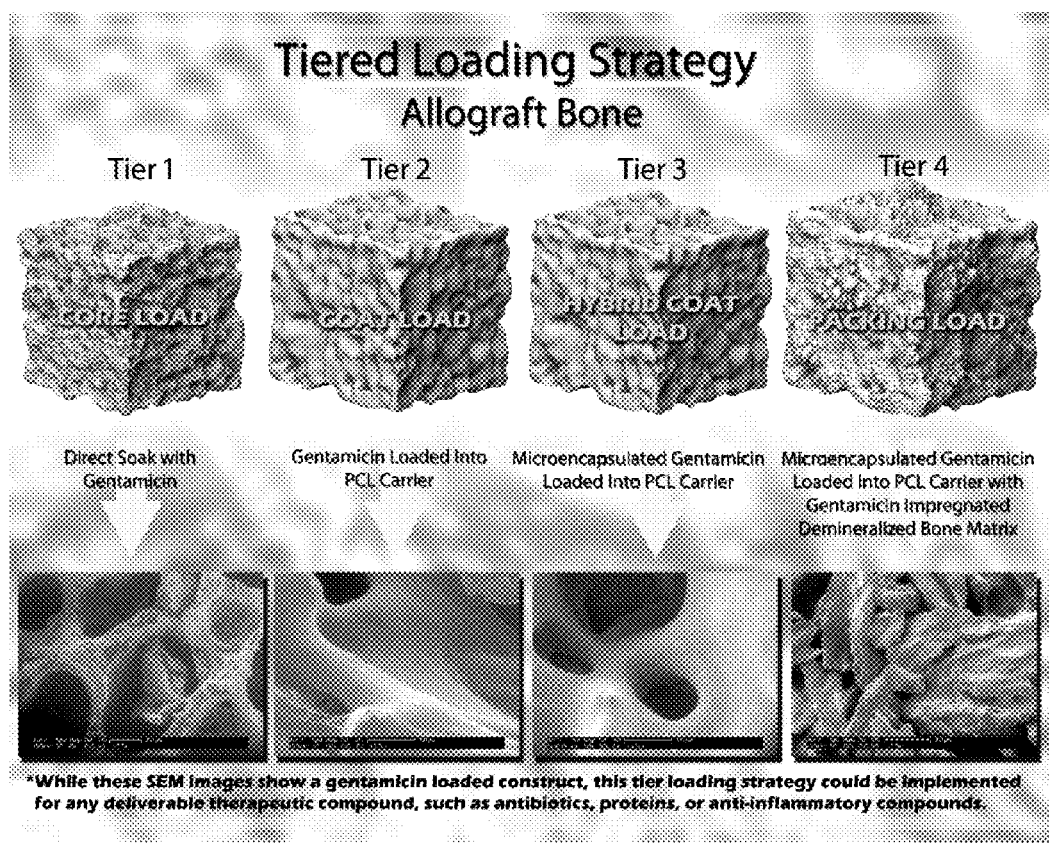
FIG. 1 is the graphical embodiment of the 'tiered' drug loading system on the graft material. This includes graft with drug 'soak' (drug adsorbed to substrate from solution only), graft with drug carried within the coated polymer rate-controlling release matrix, encapsulated drug within the coated polymer rate-controlling release matrix, and graft croutons with drug carried within the coated polymer rate-controlling release matrix mixed into a demineralized bone matrix (DBM) graft material, forming a composite. The diverse versatility of the drug loading scheme on and within the substrate and the polymer rate-controlling matrix, in addition to tunability of the rate-determining polymer release coating (release barrier), allow variable, application-specific drug loading, dosing and drug release profiles of multiple agents to be fabricated into a tissue graft biomaterial for multiple therapeutic functions.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, biomaterials, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance may or may not occur, and that the description includes instances where said event or circumstance occurs and instances where it does not.

As used herein, the term "treatment" refers to the medical management of a patient with the intent to produce a therapy, cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a tissue defect" means having been subjected to a physical examination by a person of skill, for example, a physician, and found to have a condition that can be diagnosed or treated by a tissue graft combination biomaterial.

As used herein, the phrase "identified to be in need of treatment for a disorder," or the like, refers to selection of a subject based upon need for treatment of the disorder. For example, a subject can be identified as having a need for treatment of a tissue defect (e.g., a bone defect) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a disclosed combination biomaterial to a subject. Administration can be by way of introduction of a combination biomaterial into a subject. For example, administration can be introduction via surgical implantation or injection. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired therapeutic result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to both to the polymer coating over the graft biomaterial combination substrate (e.g., pieces, croutons, morsels, super-micron and sub-micron particles, nanoparticles) that is carrying the drug(s) on the substrate, and to sterile aqueous or nonaqueous solutions, dispersions, suspensions or emulsions, as well as sterile powders or microencapsulation matrices or nanoencapsulation matrices for reconstitution into sterile injectable or coatable solutions or dispersions for incorporating drug into the polymer coating matrix. Examples of suitable aqueous and nonaqueous carriers, diluents, solvents or vehicles include water, acetone, salines, buffers, ethanol, polyols (such as glycerol, propylene glycol, polyethylene glycol and the like), carboxymethylcellulose and suitable mixtures thereof, vegetable oils (such as olive oil) and injectable organic esters such as ethyl oleate, polymeric solubilization agents including polymer surfactant micelles, and polymer carrier solutions such as those known to produce gellable depots in tissue beds, including but not limited to Pluronics and Tetronics, PEO-PLGA-PEO block copolymers, and their biocompatible gelling block copolymers analogs. Proper fluidity can be maintained, for example, by the use of coating materials excipients such as polymer mixtures, added salts or solutes, or lipids (lecithins), by the maintenance of the required particle size in the case of microencapsulated or nanoencapsulated drug dispersions, added excipients or salts, and by the use of surfactants. These compositions can also contain excipients such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and other dissolved tonicity solutes. Injectable depot forms are made by forming microencapsulated or nanoencapsulated matrices of the drug in degradable (e.g., degradable (e.g., biodegradable, resorbable), resorbable) polymer coatings (such as polycaprolactones, polylactide-polyglycolide homo- or co-polymers, poly(orthoesters), protein-based polymers, recombinant proteins and natural proteins, poly(tyrosines), polyphosphazenes, polyphosphates and polyphosphonates, polysaccharides, proteoglycans, hyalurons, chitosans, and chondroitins, and poly(anhydrides)) on injectable or implantable particle or solid piece dispersions of the osteoconductive biomaterial graft substrate. Depending upon the ratio of drug to polymer and the nature of the particular polymer employed (i.e., its chemistry, hydrolytic tendencies, physical structure such as crystallinity or macromolecular domains, and its molecular weight), the rate of drug release can be controlled. The term "pharmaceutically acceptable carrier" also refers to such vehicles used for those injectable forms of the invention that allow the polymer-coated drug-containing substrate as a particulate dispersion combination biomaterial to be injected into wound, implant, defect and surgical sites. This can include dispersion of the polymer-coated drug-releasing graft combination biomaterial as particles within such "pharmaceutically acceptable carriers" such as DBM, platelet-rich plasma (PRP), fibrin glues, synthetic hydrogel, alginate, hyaluron, protein, and collagen gel coatings or injectable vehicles, solutions or gels of degradable polymers, starches (for example but not exclusive to CMCs and polysaccharide derivatives) or proteins (both natural and recombinant), and injectable isotonic salines common to pharmaceutical injectable formulations. Depot-injectable formulations are also prepared by entrapping the drug(s) in lipid nanoparticles, surfactant phases, liposomes or surfactant microemulsions or nanoemulsions, and depot-forming polymer-solvent carriers as drug vehicles that are compatible with body tissues, and incorporating these formulations into polymer coatings over the graft biomaterial substrate.

As used herein, the term "biologically active agent" or "bioactive agent" means an agent that is capable of providing a local or systemic biological, physiological, or therapeutic effect in the biological system to which it is applied. Osteoinductive examples include but are not limited to transforming growth factors (TGFs), bone morphogenetic proteins (BMPs), fibroblast growth factors (FGFs), parathyroid hormone derivatives (PTHs), Nell-1, statins, certain known osteoinductive peptides (e.g., P15, truncated PTHs or collagens), insulin-like growth factors (IGFs), and/or platelet-derived growth factors (PDGFs), or their respective therapeutic nucleotide transgenes.

As used herein, the term "pharmaceutically active agent" includes a "drug" or a "therapeutic agent" and means a molecule, group of molecules, complex or substance administered to an organism for diagnostic, therapeutic, preventative medical, or veterinary purposes. This term includes externally and internally administered topical, localized and systemic human and animal pharmaceuticals, treatments, remedies, nutraceuticals, cosmeceuticals, biologicals, biomaterials, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term includes, but is not limited to, RNAi technologies and reagents, transgenes, protein growth factors, antimicrobials, antibiotics, microcidals, antiseptics, antifungals, anti-inflammatories, anesthetics, and analgesics. This term may also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA) or ribonucleic acid (RNA) as genetic materials introduced to produce a desired therapeutic effect.

As used herein, the term "osteoinduction" refers to the ability to stimulate the proliferation and differentiation of progenitor and partially differentiated cell types involved in initiating and completing bone formation and its tissue regeneration, including, but not limited to, exogenous pluripotent cells, mesenchymal MSC, satellite-derived muskuoloskeletal SDMSC, adipose-derived ADSC, induced pluripotent (iPS), and endogenously sourced stem cells (including MSCs, ADSC, SDMSC, both circulating and tissue resident). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct endogenous mechanisms. Direct recruitment of other differentiated cell types involved in bone formation is also significant to healing, including differentiated microvascular and endothelial cells, mural cells and pericytes, osteoblasts, chondrocytes, chondroblasts, osteoclasts, and osteocytes. Osteoinduction can be stimulated by osteogenic growth factors such as those mentioned above, although some ECM proteins also drive progenitor cells toward the osteogenic phenotype.

As used herein, the term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material and ability to produce effective therapies in these sites.

As used herein, the term "osteogenic" refers to the intrinsic ability of a graft biomaterial to produce bone in the host site. To have direct osteogenic activity, the graft must contain or elicit cellular components that directly induce bone formation and regeneration. For example, an implanted collagen matrix pre-seeded with activated MSCs would have the potential to induce bone formation directly, without recruitment and activation of host MSC populations. Because many osteoconductive scaffolds also have the ability to bind and deliver bioactive molecules, their osteoinductive potential will be greatly enhanced. Therefore combinations of osteoconductive and osteoinductive materials and agents can be used for bone regenerative purposes.

As used herein, the term "allograft" refers to a graft of tissue obtained from a donor of the same species as, but with a different genetic make-up from, the recipient. This term includes a non-living, non-viable, processed cadaveric tissue transplant between two humans.

As used herein, the term "autologous" refers to being derived or transferred from the same individual's body, such as for example an autologous bone marrow transplant.

As used herein, the term "autograft" refers to a graft of tissue obtained from an undamaged area of the patient or identical twin.

As used herein, the term "xenograft" refers to tissue or organs from an individual of one species transplanted into or grafted onto an organism of another species, genus, or family.

As used herein, the term "alloplastic" material refers to material originating from a nonliving source. The term therefore includes inorganic materials.

As used herein, the term "biomaterial" is any material, natural or man-made, that comprises whole or part of a living structure or biomedical device which performs, augments, or replaces a natural function.

As used herein, the term "combination biomaterial" refers to a composition of matter comprising two or more biomaterials serving unique therapeutic functions. The term includes a drug-releasing system in combination with a biomaterial used for a purpose other than drug delivery. Thus the term includes an implantable biomaterial serving two functions in the host: one as an implant with biomaterial function (graft material for substituting for bone and growing new bone), and the second as a controlled release drug delivery biomaterial to enhance the performance of this biomaterial in its context in situ (see Wu, Grainger, Biomaterials, 27, 2450-2467, 2006).

As used herein, the term "microspheres" shall mean generally spherical drug-loaded particles 1 µm-100 µm in size. Microspheres comprise a hollow space encapsulated by lipids, polymers, at least one surfactant, or any combination thereof, wherein the hollow space contains therapeutic agent. As used, herein, microspheres can be used to place and release drug within the polymer rate-controlling membrane to enhance drug loading, prolong and control drug dosing and extend release.

As used herein, the term "microencapsulated" refers to the enclosure of a therapeutic agent (e.g., drug) into carrier particles of about 1 µm-100 µm in size. Therapeutic agents and drugs can be encapsulated by lipids, sugars, polymers, or inorganic solids, or any combination thereof, wherein the microencapsulating matrix acts to hinder drug dissolution and release. The term "nanoencapsulated" refers to this same process of coating or encapsulating drug particles but is distinguished by the coated drug particles being sized below 1 µm, e.g., 10 nm to 1000 nm in size.

The terms "biodegradation," "bioabsorption," and "bioerosion" are often used to connote different functional processes and definitions of biomaterial degradation, dissolution and removal from the implant site. In biodegradation, a biological agent like an enzyme, cell or a microbe is the dominant component in the degradation process. Degradable (e.g., biodegradable, resobrable) implants are usually useful for short-term or temporary applications. Bioresorption and bioabsorption imply that the degradation products are removed by cellular activity, such as phagocytosis, in a biological environment. By contrast, a bioerodible polymer is a water-insoluble polymer that has been converted under physiological conditions into water-soluble materials. This occurs regardless of the physical or chemical mechanism involved in the erosion process, and can include general auto-catalyzed, base or acid catalyzed hydrolysis of the polymer. Thus, where the term "degradable" is used herein, one or more of the terms "resorbable," "degradable (e.g., biodegradable, resobrable)," "bioabsorbable," and "bioerodable" are also disclosed.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituent.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$) OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —$OC(O)A^1$ or —$C(O)OA^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -$(A^1O(O)C-A^2-C(O)O)_a$— or -$(A^1O(O)C-A^2-OC(O))_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -$(A^1O-A^2O)_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

The term "organic residue" defines a carbon containing residue, i.e., a residue comprising at least one carbon atom, and includes but is not limited to the carbon-containing groups, residues, or radicals defined herein above. Organic residues can contain various heteroatoms, or be bonded to another molecule through a heteroatom, including oxygen, nitrogen, sulfur, phosphorus, or the like. Examples of organic residues include but are not limited to alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms "Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

As used herein, the term "polymer" refers to a relatively high molecular weight organic compound, natural or synthetic, whose structure can be represented by a repeated small unit, the monomer (e.g., polyesters, polyamides, polyvinyls, polyanhydrides, polyorthoesters, polyaminoacids, polyalkenes, polyacrylates, polyarylates, polyolefins, polyacrylamides, polysugars, polyphosphonates, polyphosphazenes, polytyrosines, polyethers, polyurethanes, polycarbonates). Synthetic polymers are typically formed by addition or condensation polymerization of monomers. Natural polymers (biopolymers) include collagens and gelatins, silks, keratins, elastins, and their recombinant polymers and peptides, and peptide-polymer combinations, nucleic acids and their derivatives, starches including cellulose derivatives, chitosans, alginates, polyhydroxyalkanoates, glycosaminoglycans, proteoglycans, fibrin glues and fibrinogen derivatives for this purpose.

As used herein, the term "copolymer" refers to a polymer formed from two or more different repeating units (monomer residues, such as PLA-PLGA glycolide-lactide copolymers). By way of example and without limitation, a copolymer can be an alternating copolymer, a random copolymer, a block copolymer (e.g., Pluronics), or a graft copolymer. It is also contemplated that, in certain aspects, various block segments of a block copolymer can themselves comprise copolymers. These blocks can impart specific chemical and physical properties important to their use herein, such as depot forming properties in tissues as rate-limiting release barriers, control of polymer degradation, solubilization of drugs, and control of drug-particle encapsulate size (micro and nano encapsulates).

As used herein, the term "molecular weight" (MW) refers to the mass of one molecule of that substance, relative to the unified atomic mass unit u (equal to 1/12 the mass of one atom of carbon-12).

As used herein, the term "number average molecular weight" ($M_n$) refers to the common, mean, average of the molecular weights of the individual polymers. $M_n$ can be determined by measuring the molecular weight of n polymer molecules, summing the weights, and dividing by n. $M_n$ is calculated by:

$$\overline{M}_n = \frac{\sum_i N_i M_i}{\sum_i N_i},$$

wherein $N_i$ is the number of molecules of molecular weight $M_i$. The number average molecular weight of a polymer can be determined by gel permeation chromatography, viscometry (Mark-Houwink equation), light scattering, analytical ultracentrifugation, vapor pressure osmometry, end-group titration, and colligative properties.

As used herein, the term "weight average molecular weight" ($M_w$) refers to an alternative measure of the molecular weight of a polymer. $M_w$ is calculated by:

$$\overline{M}_w = \frac{\sum_i N_i M_i^2}{\sum_i N_i M_i},$$

wherein $N_i$ is the number of molecules of molecular weight $M_i$. Intuitively, if the weight average molecular weight is w, and you pick a random monomer, then the polymer it belongs to will have a weight of w on average. The weight average molecular weight can be determined by light scattering, small angle neutron scattering (SANS), X-ray scattering, and sedimentation velocity.

As used herein, the terms "polydispersity" and "polydispersity index" refer to the ratio of the weight average to the number average ($M_w/M_n$).

The term "pharmaceutically acceptable" describes a material that is not biologically or otherwise undesirable, i.e., without causing an unacceptable level of undesirable biological effects or interacting in a deleterious manner, and which allows both formulation and delivery of biologically active and pharmaceutically active agents to produce a desired therapy without clinically unacceptable effects.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural and chemical and pharmaceutical requirements for performing the disclosed therapeutic functions, and it is understood that there are a variety of structures, chemistries, materials and pharmaceutical embodiments that can perform the same function that are related to the disclosed structures, and that these structures will typically achieve the same desired result.

B. TISSUE GRAFT COMBINATION BIOMATERIAL

Disclosed herein are tissue graft combination biomaterials comprising one or more agents, including bioactive agents, pharmaceutically active agents, or combinations thereof. The disclosed tissue graft biomaterials can in some aspects release one or more agents at the tissue graft implantation site. In some aspects, the agent release is a controlled, extended release. Thus, also disclosed are methods of making the disclosed tissue grafts to select the rate of controlled release of bioactive agents, pharmaceutically active agents, or combinations thereof to produce therapy at the implant site.

The tissue graft biomaterials disclosed herein can be combination biomaterials of one or more agents and one or more substrates suitable for use as tissue graft materials. The one or more biomaterial substrates can generally be selected based on the target tissue and the intended biomaterial use. For example, wherein the target tissue is bone, the substrate can be a material suitable for use as a bone graft or bone filler, including but not limited to natural bone (e.g., autologous bone, allograft bone, xenograft bone), demineralized bone matrix (DBM), and alloplastic (i.e., inorganic, synthetic) graft materials (e.g., tricalcium phosphate, calcium sulfate, and hydroxyapatite, and their various physical and chemical forms, mixtures and compositions).

Thus, disclosed herein is a combination tissue graft biomaterial comprising a biocompatible substrate; a degradable natural or synthetic polymer coated over the substrate surface; and a bioactive agent or pharmaceutically active agent encapsulated by the polymer matrix. As disclosed herein, the polymer can act as a chemical solubilizer, matrix compatibilizer, and physical carrier for loading and holding the agent(s) on the device, and a rate-controlling matrix for agent(s) release.

By "encapsulated" is meant that the agent(s) can be either incorporated into the polymer or into or onto the substrate and covered by the polymer coating, such that release of the agent(s) from the combination tissue graft biomaterial is hindered and controlled by the polymer coating barrier and its degradation at the site of application. Also as disclosed herein, one or more agent(s) can be further encapsulated within microspheres or nanospheres or particles prior to loading onto the substrate or into the polymer coating. Thus, the agent(s) can be both (1) microencapsulated by microspheres, nanospheres, or other agent-particle formulations, and (2) macro-encapsulated by the disclosed polymer (e.g., within or beneath the polymer coating), thus providing two tiers of loading, dosing and release control for selected agent(s).

1. Substrate

In some aspects, the disclosed tissue graft biomaterials can be used as a bone graft. Thus, in some aspects, the biocompatible substrate is osteoinductive or osteoconductive. Thus, in some aspects, the biocompatible substrate is allograft materials intended for skeletal and bone defect grafting and implant sites.

In some aspects, the substrate comprises natural bone. In some aspects, the substrate comprises bone particles, bone powder, bone putty, or a bone fragments. In a preferred aspect, the substrate comprises fragments (also referred to herein as particles, chips, morsels, croutons) of cancellous bone.

The bone can be from any suitable natural source. Thus, in some aspects, the substrate comprises allograft bone. In some aspects, the substrate comprises autograft bone. In some aspects, the substrate comprises xenograft bone.

In some aspects, the substrate comprises a synthetic or alloplastic material. For example, in some aspects, the substrate comprises hydroxyapatite (U.S. Pat. No. 5,164,187). Hydroxyapatite materials can be in either a hydroxyapatite ceramic material or in a nanocrystalline hydroxyapatite form. In some aspects, the substrate comprises tricalcium phosphate. In some aspects, the substrate comprises medical grade calcium sulfate. In some aspects, the substrate comprises gelatin or collagen gels, or proteins (recombinant or purified natural) extracted from tissues, or a composite of suspended fibrillar collagen and a porous calcium phosphate ceramic. Providing substrates are well known by those of skill in the art. The following patents are incorporated by reference in their entirety as method of teaching how to make a bone graft substrate using hydroxyapatite (US Patent Application No. 2009/0048358), tricalcium phosphate (U.S. Pat. No. 6,846,853), medical grade calcium sulphate (European Patent No. 1390086), suspended fibrillar collagen and a porous calcium phosphate ceramic (European Patent No. 0243178).

Autogenous bone grafting involves harvesting the patient's own bone from a part of the body where it is not essential (typically from the pelvis or iliac crest), and transplanting it for therapeutic effect. Autogenous bone grafts are considered the gold standard due to immunologically seamless integration. Additionally, the graft has the most abundant "amount of the patient's bone growing cells and proteins" and is a kind of "outline" for repair and new bone growth. Unfortunately, this level of osteointegration requires the surgeon to make additional incisions to harvest the autologous bone graft; consequently, inflicting additional tissue trauma, postoperative pain, and surgical costs. Autologous bone is typically harvested from intra-oral sources as the chin or extra-oral sources as the iliac crest, the fibula, the ribs, the mandible and even parts of the skull.

All bone requires a blood supply. Depending on where the transplant site is and the size of the graft, an additional newly recruited blood supply may be required. For these types of grafts, extraction of the part of the periosteum and accompanying blood vessels along with donor bone is required. This kind of graft is known as a free flap graft.

Allograft bone grafting is similar to the autogenous bone graft in that the implanted graft material is still harvested from people; however, allograft bone is extracted from cadaveric bone donors; it is typically sourced from a bone bank. The bone is disinfected, deceullarized, deproteinated, and then frozen or lyophilized (freeze-dried). Allograft material minimizes problems associated with autograft material and takes the place of a bone graft extender or replacement in the procedure. Unfortunately, this type of graft is typically not very successful. It is fairly useful in several types of spinal fusions, but because it is not a very powerful "biological stimulant," it cannot, when used as the only grafting material, typically achieve a good fusion in procedures such as a lumbar spinal fusion.

Xenograft bone substitute has its origin from a species other than human, such as bovine. Xenografts are usually only distributed as a calcified matrix.

Alloplastic grafts may be made from hydroxyapatite, a naturally occurring mineral with many possible chemical and physical manifestations that is also the main mineral component of bone. They may also be made from bioactive glass. Hydroxyapatite is a synthetic bone graft, which is now the most commonly used synthetic graft due to its strong osteoconduction capabilities, hardness and bone compatibility. Calcium carbonate has also been used historically; however, its usage starting to decrease due to its short resorption time, which leaves the resultant bone fragile. Finally, tricalcium phosphate, which now used in combination with hydroxyapatite in mixed granular and block forms, gives both effective osteoconduction and resorbability.

In some aspects, the substrate is porous. Thus, in some aspects, the substrate has an average pore size of from about 100 µm to about 500 µm, including about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 µm. In some aspects, the substrate has interconnections of at least about 100 µm, including at least about 110, 120, 130, 140, 150, 160, 170, 180, 190, 200, 210, 220, 230, 240, 250, 260, 270, 280, 290, 300, 310, 320, 330, 340, 350, 360, 370, 380, 390, 400 µm.

In some aspects, the degradable polymer coating or membrane is coated on and upon and contiguously over the graft substrate surface as a rate-controlling barrier or membrane, substantially blocking the substrate's pores and interconnections and communications with the ambient.

2. Demineralized Bone Matrix

In some aspects, the disclosed combination biomaterial further comprises demineralized bone matrix (DBM). For example, DBM can be packed into the pores of the disclosed substrate. Alternatively, the polymer-coated drug-loaded graft materials can be dispersed and suspended as micron or smaller particulates or emulsified or encapsulated forms within DBM matrices acting as a carrier. For example, bone powder sprayed with a polymer coating can be mixed with DBM to form a composite paste.

In some aspects, the DBM can further comprise a bioactive agent or pharmaceutically active agent. Thus, agents can be released from the disclosed combination biomaterials from both the polymer coating on the graft substrate, and from the DBM, providing a two-phase release of different active agents.

Demineralized Bone Matrix (DBM) is the bioactive, proteinaceous constituent of processed cadaveric bone after removal of the inorganic, ceramic component. It is rich in osteoinductive signaling proteins, peptides, growth factors and cytokines, such as the BMPs. This is in addition to the collagenous extracellular matrix proteins that provide their own bioactive properties and give the paste-like material its packable characteristics and enhanced osteoinductive potential. Relevant cell types of mesenchymal lineage (namely osteoblasts) demonstrate a strong propensity to attach and migrate along collagen matrices and respond to gradients of BMPs and other osteogenic factors in such matrices.

DBM is inherently derived from cadaveric bone, making availability limited to qualified orthopaedic surgeons only. It is typically available from commercial vendors that carry allograft bone, such as Wright Medical, Synthesis, etc., and is often advertised as a sister product.

DBM compositions can be prepared from multiple different DBM preparations, each of which contains DBM particles of different size and/or including different amounts or types of agents.

The disclosed combination of biomaterials also provides systems and reagents for preparing and applying DBM grafts, as well as systems and reagents for treating bone defects using DBM implants. For example, the DBM composition can be provided as a paste in a delivery device such as a syringe. Preferably, the DBM composition is sterile and is packaged so that it can be applied under sterile conditions (e.g., in an operating room).

DBM can be human DBM, rat DBM, or DBM from another animal such as a cow, a horse, a pig, a dog, a cat, a sheep, or another socially or economically important animal species. In some aspects, the DBM is delipidated, such as by extraction treatment with a chloroform-methanol mixture.

3. Polymer

In one aspect, the polymer can serve at least two functions in the disclosed tissue graft combination biomaterials. First, the polymer can serve as a cohesive material that facilitates drug dosing and loading, distribution and physical and chemical compatibilization by binding, stabilizing and incorporating the biologically active and/or pharmaceutically active agent(s) to the substrate material(s) for eventual release. Second, the polymer can serve as a rate-controlling barrier mechanism for controlled release of the agent(s) from the polymer or from beneath the polymer adjacent to the substrate after introduction into a subject. In a further aspect, the polymer chemical structure, physical structure of the coating (such as aggregation states with drugs, matrix coating crystallinity, and its domain morphology), and/or polymer molecular weight and degradation mechanisms and rates can be selected to serve these functions, offering a level of tunability for controlling and extending drug release not possible with other technologies.

In several aspects, suitable polymers can be obtained commercially. For example, various polycaprolactone formulations can be obtained from Solvay Chemicals or Lactel (Pelham, Ala.) or Sigma Aldrich in St. Louis, Mo. (Catalog numbers 440752, 440744)

In further aspects, those of skill in the art can readily prepare polymers and copolymers by radical initiation or condensation or recombinant, vector-based synthesis of monomers corresponding to the desired polymer residues.

It is understood that the polymer can be provided as a solution, emulsion or suspension in a solvent or with surfactant stabilization, for example, during spray coating.

In some aspects synthetic polymers can be used. The following are examples of synthetic polymers: (including but not exclusive to) polyesters, polyamides, polyvinyls, polyanhydrides, polyorthoesters, polyaminoacids, polyalkenes, polyacrylates, polyarylates, polyolefins, polyacrylamides, polysugars, polyphosphonates, polyphosphazenes, polytyrosines, polyethers, polyurethanes, polycarbonates.

In some aspects natural polymers can be used. The following are examples of natural polymers: (including but not exclusive to) collagens and gelatins, silks, keratins, elastins, and their recombinant polymers and peptides, and peptide-polymer combinations, nucleic acids and their derivatives, starches including cellulose derivatives, alginates, polyhydroxyalkanoates, glycosaminoglycans, proteoglycans, fibrin glues and fibrinogen derivatives.

a. Structure

In some aspects, the polymer comprises monomer residues, wherein at least about 50% of the monomer residues have a structure represented by a formula:

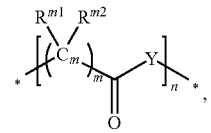

wherein m is an integer from 1 to 12; wherein n is an integer selected to yield a molecular weight of the polymer from about 5 kD to about 450 kD, including from about 5 kD to about 300 kD, from about 5 kD to about 200 kD, and from about 5 kD to about 100 kD; wherein Y is or N—R, wherein R is hydrogen, optionally substituted alkyl, or optionally substituted aryl; and wherein each of $R^{m1}$ and $R^{m2}$ is independently hydrogen, halogen, hydroxyl, nitrile, nitro, thiol, optionally substituted amino, and optionally substituted organic residue. As used herein, "kD" refers to kilodaltons, or 1000 Daltons, or 1000 grams/mo.

It is contemplated that such structures can be represented such that, if m is 1, m1 represents 11, and $R^{m1}=R^{11}$. Likewise, if m is 2, m1 represents 11, m2 represents 21, m3 represents 31, and $R^{11}$, $R^{12}$, $R^{21}$, and $R^{22}$ are present in the residue structure. Thus, wherein m=3, a polymer can comprise a residue having a structure represented by a formula:

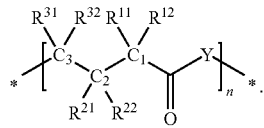

In some aspects, at least about 50% of monomer residues in the degradable polymer have a structure represented by a formula:

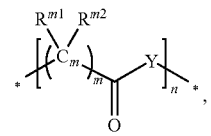

wherein m is an integer from 2 to 8; wherein n is an integer selected to yield a molecular weight of the polymer of from about 10 kD to about 450 kD, including from about 10 kD to about 300 kD, from about 10 kD to about 200 kD, and from about 10 kD to about 100 kD; wherein Y is O or N—R, wherein R is hydrogen, optionally substituted alkyl comprising from 1 to 6 carbons, or optionally substituted aryl comprising from 1 to 6 carbons; and wherein each of $R^{m1}$ and $R^{m2}$ is independently hydrogen, halogen, hydroxyl, nitrile, nitro, thiol, optionally substituted amino, and optionally substituted organic residue comprising from 1 to 6 carbons.

In some aspects, at least about 75% of monomer residues in the degradable (e.g., degradable (e.g., biodegradable, resobrable), resobrable) polymer have a structure represented by a formula:

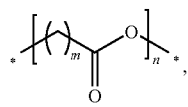

wherein m is an integer from 2 to 8; and wherein n is an integer selected to yield a molecular weight of the polymer of from about 10 kD to about 80 kD.

In some aspects, at least about 75% of monomer residues in the degradable and resorbable polymer comprise caprolactone residues. In some aspects, the degradable polymer of the disclosed combination biomaterial is a polyester. In some aspects, the polyester is polycaprolactone. In some aspects, the polyester further comprises polylactic acid, polyglycolic acid and/or D, L-polylactide-co-glycolide (PLGA). In some aspect, the polymer can be selected from a diverse, recognized set of biomaterials, including DBM, platelet-rich plasma (PRP), fibrin glues, nucleic acids, alginates, hydrogels, gelatins and collagen gel coatings, degradable polymers such as polyanhydrides, polytyrosines, polyaminoacids, polyphosphonates, polyorthoesters, polysaccharides and chitosans, glycosaminoglycans, starches (for example but not exclusive to CMC), hyaluronic acids or chondroitins, heparins or proteins (albumin, fibrinogen, silk, collagen and many others).

In various aspects, each of R group (e.g., $R^{m1}$ and $R^{m2}$) can be independently hydrogen, halogen, hydroxyl, nitrile, nitro, thiol, optionally substituted amino, and optionally substituted organic residue.

In some aspects, the polymer has a structure and a molecular weight selected to degrade over a time period when implanted within a subject and thereby release the agent(s) over the designated therapeutic time period. In some aspects, the time period is at least about one day. In some aspects, the time period is at least about 1, 2, 3, 4, 5, 6, 7, 8, 9, 10, 11, 12, 13, 14, 15, 16, 17, 18, 19, 20 days. In some aspects, the time period is at least about one week. In some aspects, the time period is at least about two weeks. In some aspects, the time period is at least about three weeks. In some aspects, the time period is at least about four weeks. In some aspects, the time period is at least about five weeks. In some aspects, the time period is at least about six weeks.

b. Molecular Weight

When referring to molecular weight, it is understood that those of skill in the art typically refer to number average molecular weight ($M_n$) or weight average molecular weight ($M_w$).

As disclosed herein, the rate of release can be selected by modulating the molecular weight of the disclosed polymer coating materials. Thus, in some aspects, the tissue graft combination biomaterials provide a "tier 2" release as shown in FIG. 1. Thus, in some aspects, the polymer has a molecular weight of from about 5 kD to about 450 kD. Thus, in some aspects, the polymer has a molecular weight of from about 5 kD to about 300 kD. Thus, in some aspects, the polymer has a molecular weight of from about 5 kD to about 200 kD. Thus, in some aspects, the polymer has a molecular weight of from about 5 kD to about 100 kD. In some aspects, the polymer has a molecular weight of from about 10 kD to about 80 kD. In some aspects, the polymer has a molecular weight of about 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 160, 170, 180, 190, 200 190, 200, 210, 220, 230, 240, 250, 260, 270, 280, 290, 300, 310, 320, 330, 340, 350, 360, 370, 380, 390, 400, 410, 420, 430, 440, 450 kD.

4. Microencapsulation

In some aspects, the agent(s) is/are encapsulated (e.g., microencapsulated, nanoencapsulated) as particle formulations (e.g., microspheres, nanospheres) prior to being macroencapsulated by polymer coating (i.e., loaded within or beneath the polymer coating). These encapsulated particle drug forms can then be loaded onto the biomaterial substrate by direct adsorption, impregnated into the substrate using a viscous matrix such as DBM, by suspension within the polymer coating, and in combinations with free un-encapsulated drug. Thus, in some aspects, the tissue graft combination biomaterials provide a further desired and designed "tier 3" loading and release capability as shown in FIG. 1. Particle encapsulation involves packaging an active ingredient (e.g., drug) inside a solid-phase capsule ranging in size from about one micron to several millimeters for microencapsulation and from about 10 nm to about 1000 nm for nanoencapsulation. The solid encapsulate matrix capsule protects the active drug or bioactive ingredient from its surrounding environment until an appropriate time when the solid allows its release through various mechanisms. Then, the drug or bioactive material escapes through the capsule wall by various means, including hydrolysis and rupture, degradation, carrier dissolution, melting or diffusion to be released.

In some aspects, the agent is microencapsulated in a microcapsule or microsphere. U.S. Pat. No. 6,224,794 is incorporated by reference herein in its entirety for its teaching of how to make and use microspheres for microencapsulation of agents. Degradable (e.g., biodegradable, resorbable) microcapsules, containing one or more drugs can be prepared by methods known in the art (see Microencapsulation: Methods and Industrial Application, ed. by Simon Benita, Marcel Dekker, Inc. New York, 1996, which is hereby incorporated by reference in its entirety for its teaching of how to microencapsulate bioagents). Particularly useful are microcapsule formulations which are stable at pH levels below about 9 and which lyse or release at pH above about 9. By controlling these pH variations, drug release will be controlled at and limited to the site where appetite is being formed. Hydrolytically and dissolution controlled release from microencapsulated forms can also be used with slowly dissolving or degrading capsule solids as the matrix. U.S. Pat. No. 6,716,450 is incorporated by referenced herein for the teaching of fabrication methods and properties for nanocapsules useful for encapsulating bioactive molecules such as proteins and drugs. These nanocapsules comprise branched or hyperbranched polymers and copolymers and have a core-shell structure forming a capsule volume appropriate for complexing and retaining growth factors and other bioactive molecules. The nanoencapsulated bioactive molecule is stable in extreme temperatures and pH, soluble in aqueous or organic solvents, and can be lyophilized to a dry powder for long-term storage without loss of activity.

5. Agents

The bioactive agent(s) or pharmaceutically active agent(s) of the herein disclosed compositions and methods can be any such agent suitable for administration to a tissue graft site. In some aspects, the bioactive agent or pharmaceutically active agent is selected to promote tissue graft incorporation, promote tissue regeneration, prevent infection, or any combination thereof. For example, the bioactive or pharmaceutically active agent(s) can act to: control infection and inflammation; enhance cell growth and tissue regeneration; control tumor growth; act as an analgesic or anesthetic; promote anti-cell attachment; enhance bone growth; hinder osteoporosis; and enhance local anabolic or metabolic tissue functions, among other functions. Bioactive agents include prodrugs, which are agents that are not biologically active when administered but, upon administration to a subject are converted to bioactive agents through metabolism, enzymes or some other mechanism. Additionally, any of the compositions of the invention can contain combinations of two or more bioactive and pharmaceutical agents.

In some aspects, the bioactive agent or pharmaceutically active agent is present in the combination biomaterial in an amount necessary to provide a therapeutically effective dosage over at least one week as an extended release formulation. In some aspects, the bioactive agent or pharmaceutically active agent is present in the combination biomaterial in an amount necessary to provide a therapeutically effective dosage over at least two weeks. In some aspects, the bioactive agent or pharmaceutically active agent is present in the combination biomaterial in an amount necessary to provide a therapeutically effective dosage over at least three weeks. In some aspects, the bioactive agent or pharmaceutically active agent is present in the combination biomaterial in an amount necessary to provide a therapeutically effective dosage over at least four weeks. In some aspects, the bioactive agent or pharmaceutically active agent is present in the combination biomaterial in an amount necessary to provide a therapeutically effective dosage over at least five weeks. As disclosed herein, this extended agent release beyond the conventional initial bolus release of less than one week has specific therapeutic advantages for patient use.

In some aspects, the bioactive agent or pharmaceutically active agent is present in the combination biomaterial in an amount necessary to provide a therapeutically effective dosage over at least one day. In some aspects, the bioactive agent or pharmaceutically active agent is present in the combination biomaterial in an amount necessary to provide a therapeutically effective dosage over at least 1, 2, 3, 4, 5, 6, 7, 8, 9, 10, 11, 12, 13, 14, 15, 16, 17, 18, 19, 20 days. In some aspects, the bioactive agent or pharmaceutically active agent is present in the combination biomaterial in an amount necessary to provide a therapeutically effective dosage over at least one week. In some aspects, the bioactive agent or pharmaceutically active agent is present in the combination biomaterial in an amount necessary to provide a therapeutically effective dosage over at least two weeks. In some aspects, the bioactive agent or pharmaceutically active agent is present in the combination biomaterial in an amount necessary to provide a therapeutically effective dosage over at least three weeks. In some aspects, the bioactive agent or pharmaceutically active agent is present in the combination biomaterial in an amount necessary to provide a therapeutically effective dosage over at least four weeks. In some aspects, the bioactive agent or pharmaceutically active agent is present in the combination biomaterial in an amount necessary to provide a therapeutically effective dosage over at least six weeks.

Bioactive agents or pharmaceutically active agents ("agents") include the herein disclosed categories and specific examples. It is not intended that the category be limited by the specific examples. Those of ordinary skill in the art will recognize also numerous other compounds that fall within the categories and that are useful according to the invention.

It is understood that an agent can be used in connection with administration to various subjects, for example, to humans (i.e., medical administration) or to animals (i.e., veterinary administration).

In some aspects, the bioactive agent is a growth factor. It is understood that proteins such as growth factors can be naturally sourced or recombinant. In some aspects, the bioactive agent is an osteogenic growth factor. In some aspects, the bioactive agent comprises a transforming growth factor (TGF). Thus, in some aspects, the bioactive agent comprises TGF-β1. Thus, in some aspects, the bioactive agent comprises TGF-β2. Thus, in some aspects, the bioactive agent comprises TGF-β3. In some aspects, the bioactive agent comprises a bone morphogenetic protein (BMP). Thus, in some aspects, the bioactive agent comprises BMP-2. Thus, in some aspects, the bioactive agent comprises BMP-4. Thus, in some aspects, the bioactive agent comprises BMP-6. Thus, in some aspects, the bioactive agent comprises BMP-7. Thus, in some aspects, the bioactive agent comprises BMP-13. In some aspects, the bioactive agent comprises a fibroblast growth factor (FGF). In some aspects, the bioactive agent comprises an insulin-like growth factor (IGF). Thus, in some aspects, the bioactive agent comprises IGF-I. Thus, in some aspects, the bioactive agent comprises IGF-II. In some aspects, the bioactive agent comprises a platelet-derived growth factor (PDGF). Thus, in some aspects, the bioactive agent comprises PDGF-BB. In some aspects, the bioactive agent comprises a vascular endothelial growth factor (VEGF). In some aspects, the bioactive agent comprises Bone-derived growth factor-2 (BDGF II). In some aspects, the bioactive agent comprises LIM mineralization protein (LMP-1). In some aspects, the bioactive agent comprises growth differentiation factor 5 (GDF-5).). In some aspects, the bioactive agent comprises parathyroid hormone derivatives (PTH).

In some aspects, the bioactive agent or pharmaceutically active agent is an anti-inflammatory agent. Anti-inflammatory compounds include the compounds of both steroidal and non-steroidal structures. Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desoxymethasone, desoxycorticosterone acetate, dexamethasone, dichlorisone, diflucortolone valerate, fluadrenolone, fluclorolone acetonide, fludrocortisone, flumethason pivalate, fluosinolone acetonide, fluocinonide, flucortine butylesters, fluocortolone, fluprednidene (fluprednylidene) acetate, flurandrenolone, hydrocortisone acetate, hydrocortisone butyrate, methylprednisolone, triamcinolone acetonide, cortisone, flucetonide, fludrocortisone, difluorosone diacetate, fluradrenolone, fludrocortisone, difluorosone diacetate, fluocinolone, fluradrenolone acetonide, medrysone, amcinafel, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds can also be used.

Non-limiting example of non-steroidal anti-inflammatory compounds include celecoxib, nimesulide, apasone, gold, oxicams, such as meloxicam, and CP-14,304; the salicylates, such as aspirin, disalcid, benorylate, trilisate, safapryn, and solprin; the acetic acid derivatives, such as diclofenac, furofenac, acematacin, zomepirac, clindanac, oxepinac, and ketorolac; the fenamates, such as mefenamic, meclofenamic, flufenamic, niflumic, and tolfenamic acids; the propionic acid derivatives, such as fenoprofen, indopropfen, pranoprofen, miroprofen, tioxaprofen, alminoprofen, and tiaprofenic; and the pyrazoles, such as phenylbutazone, feprazone, azapropazone, and trimethazone.

Anti-inflammatory agents (e.g., Alclofenac, Alclometasone Dipropionate, Algestone Acetonide, alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Decanoate, Deflazacort, Delatestryl, Depo-Testosterone, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lornoxicam, Loteprednol Etabonate, Meclofenamate Sodium, Meclofenamic Acid, Meclorisone Dibutyrate, Mefenamic Acid, Mesalamine, Meseclazone, Mesterolone, Methandrostenolone, Methenolone, Methenolone Acetate, Methylprednisolone Suleptanate, Morniflumate, Nabumetone, Nandrolone, Naproxen, Naproxen Sodium, Naproxol, Nimazone, Olsalazine Sodium, Orgotein, Orpanoxin, Oxandrolane, Oxaprozin, Oxyphenbutazone, Oxymetholone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Sanguinarium Chloride, Seclazone, Sermetacin, Stanozolol, Sudoxicam, Sulindac, Suprofen, Talmetacin, Talniflumate, Talosalate, Tebufelone, Tenidap, Tenidap Sodium, Tenoxicam, Tesicam, Tesimide, Testosterone, Testosterone Blends, Tetrydamine, Tiopinac, Tixocortol Pivalate, Tolmetin, Tolmetin Sodium, Triclonide, Triflumidate, Zidometacin, Zomepirac Sodium).

In some aspects, the bioactive agent or pharmaceutically active agent is an antibiotic. Suitable antibiotics include, without limitation nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Thus, the bioactive agent or pharmaceutically active agent can be ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, cefotiam, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, timidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol, or any combination thereof.

In some aspects, the bioactive agent or pharmaceutically active agent is an anti-microbial peptide. Thus, the bioactive agent or pharmaceutically active agent can comprise defensin, cathelicidin, or saposin peptides and their related derivatives. Thus, the bioactive agent or pharmaceutically active agent can comprise an antimicrobial small molecule. Thus, the bioactive agent or pharmaceutically active agent can comprise benzoxazine, bipyridinium, cyanine, guanidone, naphthalimide, nitrofuran, quinazolindiamine, quinolamine, salicylanilide, or furanone or any combinations thereof.

In some aspects, the bioactive agent or pharmaceutically active agent is an anti-septic agent. Thus, the bioactive agent or pharmaceutically active agent can comprise medical alcohols (ethanol, isopropanol), chlorhexidine and related bi- and poly-guanides (e.g., PHMB), povidone iodine, triclosan and its derivatives, and cationic antiseptics including benzylakylammonium compounds, quaternary ammonium antibiotics, and antimicrobial polycations and related compounds known for anti-septic properties.

In some aspects, the bioactive agent or pharmaceutically active agent is a therapeutic antibody drug or antibody-derivative drug class agent. Thus, the bioactive agent or pharmaceutically active agent can comprise known and emerging antibody drugs as described in Dübel, Stefan (ed.), Handbook of Therapeutic Antibodies, January 2007, 1190 pages, 3 volumes, ISBN-10: 3-527-31453-9, known to produce specific, novel therapies against osteoporosis, inflammation, tumors, infection, and also promote tissue and vascular regeneration by activating novel receptor signaling pathways in tissues.

In some aspects, the bioactive agent or pharmaceutically active agent is a bisphosphonate. Thus, the bioactive agent or pharmaceutically active agent can comprise alendronate, risedronate, etidronate, ibandronate, pamidronate, zoledronate, and related compounds.

In some aspects, the bioactive agent or pharmaceutically active agent is a pro-angiogenic agent to promote therapeutic wound site angiogenesis, endothelial cell recruitment, vascular perfusion and neovascularization. Thus, the bioactive agent or pharmaceutically active agent can comprise angiogenesis promoters such as VEGF, its truncated forms and analogs, Endothelin-1, Ang-1 and -2, PDGF isoforms, and other bioactive compounds in this regard as described U.S. Pat. No. 6,284,758.

In some aspects, the bioactive agent or pharmaceutically active agent is a angiogenesis inhibitor, or anti-neoplastic or anti-tumor agent. Thus, the bioactive agent or pharmaceutically active agent can comprise any of a number of known anti-cancer drugs.

In some aspects, the bioactive agent or pharmaceutically active agent is a statin. Thus, the bioactive agent or pharmaceutically active agent can comprise lovastatin, pravastatin, simvastatin, atorvastatin, rosuvastatin, fluvastatin, and related statin derivatives.

C. METHODS OF MAKING THE COMBINATION BIOMATERIALS

In one aspect, the invention relates to methods of preparing a tissue graft combination biomaterial disclosed herein. In some aspects, the method comprises the steps of providing a biocompatible, osteoconductive, porous substrate; combining an effective amount of one or more bioactive agent or pharmaceutically active agent with the substrate; and coating the substrate surface with a degradable polymer.

In some aspects, the combining is soaking the substrate in a solution comprising the agents. In some aspects, the combining and coating steps are performed substantially simultaneously by mixing the solvated polymer with both free agents and microencapsulated nanoencapsulated agent preformulations, and coating the mixture on the substrate surface. In some aspects, the combining and coating steps are performed substantially simultaneously by soaking the substrate in drug solution, impregnating the substrate with the free or encapsulated drug, and coating the polymer containing either free or encapsulated drug particles or both over the substrate.

As disclosed herein, the tissue graft combination biomaterials disclosed herein provide multi-tiered nature of the therapeutic agent loading strategy, allowing for versatile tailoring of the drug selection, combination therapies, individual drug loadings and dosings, and controlled and extended release to the site of application to produce application- and even patient-specific treatment approaches.

For example an allograft material (e.g., biocompatible, osteoconductive, porous substrate) can be (1) soaked directly with drug (free or microencapsulated), (2) coated with a rate-controlling biodegradable, degradable or resorbable polymeric barrier coating (e.g., polycaprolactone), which can further contain a drug or drugs formulation (free, microencapsulated or nanoencapsulated, or suspended in a secondary biodegradable polymer), and/or (3) impregnated or packed into the substrate with a synthetic or natural polymer (e.g., DBM, PRP, collagen, protein gel) throughout the porous structure of the allograft that can also be loaded with one or multiple drugs in various physical and chemical forms. These three drug loading and dosing levels constitute the Primary Loading and Dosing Tiers.

Primary Loading and Dosing Tier (1) can be obtained by soaking the allograft material directly in a solution of either free or microencapsulated agent. Microencapsulation of the agent adds an additional level of loading and controlled release, and hence another tier to the graft system. The graft could then be further treated with either or both Primary Loading and Dosing Tiers (2) and (3).

Primary Loading and Dosing Tier (2) can be obtained through the polymer application strategies described herein and incorporating various drug formulations into the Tier (2) rate-controlling element itself. The agent could be free in the matrix, formulated within an interspersed microencapsulated or nanoencapsulated phase, or incorporated into a secondary polymer with a degradation rate different than that of the bulk rate modulating Tier (2) polymer. Both microencapsulation or nanoencapsulation of the agent and incorporation into a secondary differentially-degradative polymer add additional levels of controlled release, and hence additional tiers to the graft system. Allograft treated with Primary Loading and Dosing Tier (2), can also have previously been loaded under (1) and may go on to be loaded under (3), but does not necessarily require any previous or further loading; any combination is possible.

Primary Loading and Dosing Tier (3) can be obtained by packing the void space of the allograft with either synthetic or naturally derived polymer (e.g., DBM, PRP, collagen or protein or polymer gel or carrier) containing agent. For particulate allograft, the pieces can be mixed with the Tier (3) polymer to make a packable paste. For non-porous allograft, the Tier (3) can be applied as a uniform surface coat. Agent can be added to the Tier (3) in any of the forms previously described. The agent can be free in the matrix, formulated within an interspersed microcapsule phase, or incorporated into a secondary polymer with a degradation rate different than that of the bulk rate modulating Tier (3) polymer. Both microencapsulation or nanoencapsulation of the agent and incorporation into a secondary differentially-degradative polymer add additional levels of controlled release, and hence additional tiers to the graft system. Allograft treated with Primary Loading and Dosing Tier (3), can have previously been loaded under (1) and/or (2), but does not necessarily have to have received any previous loading; any combination is possible.

Refer to FIG. 1 for graphical representation of the multi-tier loading and dosing strategy.

It is advantageous to have the secondary packing polymer mentioned in Primary Loading and Dosing Tier (3) exhibit osteoinductive characteristics to encourage the infiltration of osseous healing cell phenotypes. DBM is a candidate for this purpose, being a naturally-derived heterogeneous polymer paste of bone-derived proteins that is capable of a high degree of antibiotic and/or other bioative agent loading. Degradable (e.g., biodegradable, resorbable) synthetic polymers can likewise exhibit osteoinductive potential by loading them with the appropriate bioactive molecules, such as PTH analogs, therapeutic antibodies, BMPs, VEGFs, and PDGFs, with or without microencapsulation or nanoencapsulation.

In some aspects, the polymer has a structure and a molecular weight selected to degrade over a therapeutic time period when implanted within a subject and thereby release the agent over a corresponding time period by degradation controlled kinetics.

In some aspects, the rate-controlling polymer coating is spray coated. In some aspects, the coating is applied via soaking or dip-coating methods common to the biomedical industry. In some aspects, the mixing and coating steps are performed substantially simultaneously. In further aspects, the mixing and coating steps are performed sequentially.

Also disclosed herein are the products produced by the disclosed methods.

D. KITS

In one aspect, the invention relates to kits comprising at least two combination biomaterials disclosed herein, wherein the at least two combination biomaterials comprise different bioactive or pharmaceutically active agents that can be mixed to tailor appropriate balances of each agent type in the site.

Also disclosed is a kit comprising at least one combination of biomaterial disclosed herein and instructions for introducing the combination biomaterial into a subject. The combination biomaterial of the disclosed kits can comprise a degradable (e.g., biodegradable, resorbable) polymer having at least about 75% caprolactone residues. The combination biomaterial of the disclosed kits can include one or more antimicrobial agents.

E. METHODS OF USING THE COMBINATION BIOMATERIALS

Also provided is a method of use of a disclosed tissue graft combination biomaterial. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered from multiple drugs loaded on the same grafting biomaterial substrate, or from mixing different grafting substrates each containing different agents. It is also envisioned that the combination of one or more active ingredients and a disclosed compound can be more efficacious than either as a single agent.

Disclosed herein is a method for introducing a tissue graft combination biomaterial, the method comprising the steps of providing a bioactive tissue graft combination biomaterial comprising: a biocompatible, osteoconductive, porous substrate; a degradable (e.g., biodegradable, resorbable) polymer coated on the substrate surface; and one or more bioactive agent(s) or pharmaceutically active agent(s) encapsulated by (e.g., sealed by, within or beneath) the polymer; and introducing the combination biomaterial into a subject. In some aspects, the bioactive agent(s) or pharmaceutically active agent(s) are applied either as a direct soak (tier 1 release) to be encapsulated (e.g., sealed by, within or beneath) the polymer coating, or drug captured within the polymer coating (tier 2 release). In some aspects, the bioactive agent(s) or pharmaceutically active agent(s) is microencapsulated in a microsphere or nanosphere and further encapsulated ((e.g., sealed by, within or beneath) the polymer coating (tier 3 release). In some aspects, all three tiers can be used on the same or different grafting substrates, alone or in mixtures, in applications. In some aspects of the method, the polymer has a structure and a molecular weight selected to degrade over a time period when implanted within a subject and thereby release the agent(s) over the equivalent time period by degradation-controlled release.

Also disclosed is a method for treating a tissue defect, comprising the steps of: identifying a subject having a tissue defect in need of treatment; providing a tissue graft combination biomaterial comprising: a biocompatible, osteoconductive, porous substrate; a degradable and resorbable polymer coated on the substrate surface; and one or more bioactive agent(s) or pharmaceutically active agent(s) encapsulated by (e.g., sealed by, within or beneath) the polymer; and introducing the combination biomaterial into a subject proximate to the tissue defect. In some aspects of the method, the polymer has a structure and a molecular weight selected to act as both a drug solubilizer and carrier, and also as a rate-controlling barrier for drug release with specified degradation capacity thereby releasing the agent over a designated or therapeutic time period correlated to polymer degradation.

The combination biomaterial can be any bioactive tissue graft combination disclosed herein. Thus, in some aspects, the combination biomaterial releases the agent over an about one- to about six-week period. In some aspects, the agent is an antimicrobial agent. In some aspects, the subject is a mammal. In some aspects, the subject is a human. In some aspects, introduction is surgical implantation. In some aspects, introduction is injection.

Also disclosed herein is a use of a tissue graft combination biomaterial for treating a subject having a tissue defect, the combination biomaterial comprising: a biocompatible, osteoconductive, porous substrate; a degradable polymer coated on the substrate surface; and one or more bioactive agent(s) or pharmaceutically active agent(s) encapsulated by the polymer, wherein the polymer has a structure and a molecular weight selected to degrade (e.g., biodegrade and/or resorb) over a time period when implanted within a subject and thereby release the agent over the same time period controlled by the polymer degradation. The combination biomaterial can be any tissue graft combination biomaterial disclosed herein. In some aspects, the disclosed use is for treating a tissue defect in a subject. In some aspects, the disclosed use is for releasing a bioactive or pharmaceutically active agent(s) in a subject.

It is understood that the disclosed methods can be used in connection with the disclosed compounds, compositions, kits, and uses.

The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment. In some aspects of the disclosed methods, the subject has been identified with a need for treatment prior to the administering step. In one aspect, a subject can be treated prophylactically with a compound or composition disclosed herein, as discussed herein elsewhere.

F. EXPERIMENTAL

The following examples are put forth so as to provide those of ordinary skill in the art with a complete disclosure and description of how the compounds, compositions, articles, biomaterials and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following examples. Starting materials and the requisite intermediates are in some cases commercially available, or can be prepared according to literature procedures or as illustrated herein.

1. Antibiotic Release Profiles From PCL Matrices a. Construction of Graft

Allograft cancellous croutons were cut to uniform size and weighed. Tobramycin powder was commercially microencapsulated utilizing lipid-sprayed microspheres. Six grams of polycaprolactone (PCL) were first dissolved in 150 milliliters of acetone at 47 degrees centigrade. Gentamicin powder and microencapsulated tobramycin were mixed with PCL in solution with sonication. About 6.25 mg of antibiotic was used for each bone specimen. A pressurized fine spray was used to apply the PCL solution directly to the cancellous for uniform application. Air drying for 2 hours allowed the acetone to dissipate, creating a thin coat on the bone. DBM was loaded with 40 mg/ml of gentamicin in phosphate buffered saline using syringe infusion and packed into the PCL-coated croutons for one test group.

b. Elution Phase

Four test groups (cohorts) were created, each with eight specimens. Group 1 (Control) comprised of bone croutons soaked in gentamicin solution (50 mg/ml) for 12 hrs. Group 2 (Gent) comprised of bone croutons sprayed with PCL (MW 200,000)/gentamicin solution (~50 mg/ml). Group 3 (Micro) comprised of bone croutons sprayed with PCL/microencapsulated tobramycin solution. Group 4 (DBM) comprised of bone croutons sprayed with PCL/microencapsulated tobramycin solution packed with gentamicin infused DBM (40 mg/ml). PCL is made from the following commercial process:

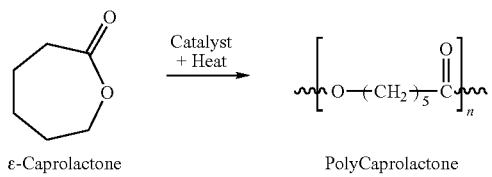

ε-Caprolactone → PolyCaprolactone

Simulated Body Fluid (SBF) was prepared according to: T. Kokubo, H. Kushitani, S. Sakka, T. Kitsugi and T. Yamamuro, "Solutions able to reproduce in vivo surface-structure changes in bioactive glass-ceramic A-W", *J. Biomed. Mater. Res.*, 24, 721-734 (1990). The following salt ions were present at the corresponding mM concentrations in 18Ω Millipore treated water: $Na^+$, [142.0]; $K^+$, [5.0]; $Mg^{2+}$, [1.5]; $Ca^{2+}$, [2.5]; $Cl^-$, [148.8]; $HCO_3^-$, [4.2]; $HPO_4^{2-}$—, [1.0]; $SO_4^{2-}$, [0.5].

Eight trials were completed on each of the four test groups by placing each specimen in 5 ml of simulated body fluid (SB F) and measuring drug release into SBF at 37° C. All release fluids for all specimens were exchanged at each of the following time intervals below: 24 hours, 72 hours, 1 week, 2 weeks, 3 weeks, 4 weeks, 5 weeks, 6 weeks.

c. Antibiotic Assay

Cobas Integra Therapeutic Drug Monitoring was used wherein R1 represents an antibody reagent, anti-gentamicin or anti-tobramycin monoclonal antibody (mouse), in buffer, ph 7.5, with stabilizer and preservative. R2+SR represents the tracer reagent, fluorescein-labeled gentamicin derivative in buffer, pH 8.5, with stabilizer and preservative. Fluorescence polarization was used for the quantitative determination of drug concentrations in simulated body fluid for the purpose of drug monitoring.

d. Bacterial Suppression Study

Thirty two agar petri dishes were set up with blood agar medium. *Escherichia coli* was used as the inoculum. 0.4 ml of inoculum was spread over the surface of each agar plate using rolling glass beads. Cancellous crouton specimens (labeled 1-32) were placed in the center of the agar-containing petri dishes. All dishes were kept in an upright position until the inoculum was absorbed (about 10 minutes). All dishes were then incubated for 45-48 hours at 37° C. Zone of inhibition was then recorded for each sample petri dish and the measurement was recorded as (1) distance of clear space from the edge of bone in mm and (2) the radius of the bone graft.

e. Release Profiles

Release profile experiments were performed as follows: cancellous bone chips treated to the prescribed regimens were allowed to release drug into a 5 ml volume of simulated body fluid (SBF) for the eight assigned time points out to 6 weeks. Release fluid was replaced at every time point and saved for drug quantification analysis using FPIA (Fluorescence Polarization Immunoassay).

f. Results

Figure 2:
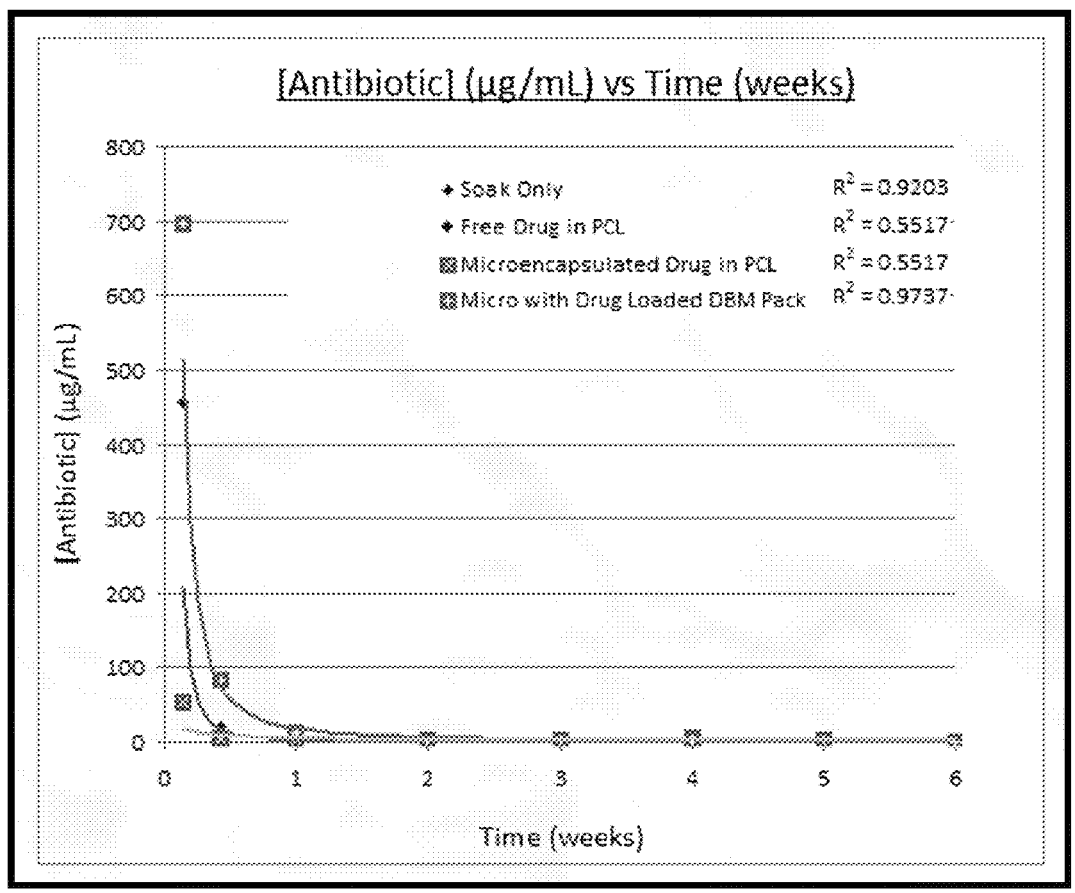
FIG. 2 shows in vitro gentamicin drug release profiles from different preparations of antibiotic-loaded allograft for 24 hr, 72 hr, and 1-through 6-week time points. All samples exhibit initial bolus drug release desired for initial anti-microbial therapy in the local environment around the graft. Biomaterial samples without a polycaprolactone (PCL) polymer controlled release coating are exhausted of their drug payload essentially after 1 week. Biomaterial samples with a polycaprolactone (PCL) polymer controlled release coating continue to release drug well beyond 1 week. All curves are power-fit. See FIG. 3 for release profiles beyond the bolus release regime.
Figure 3:
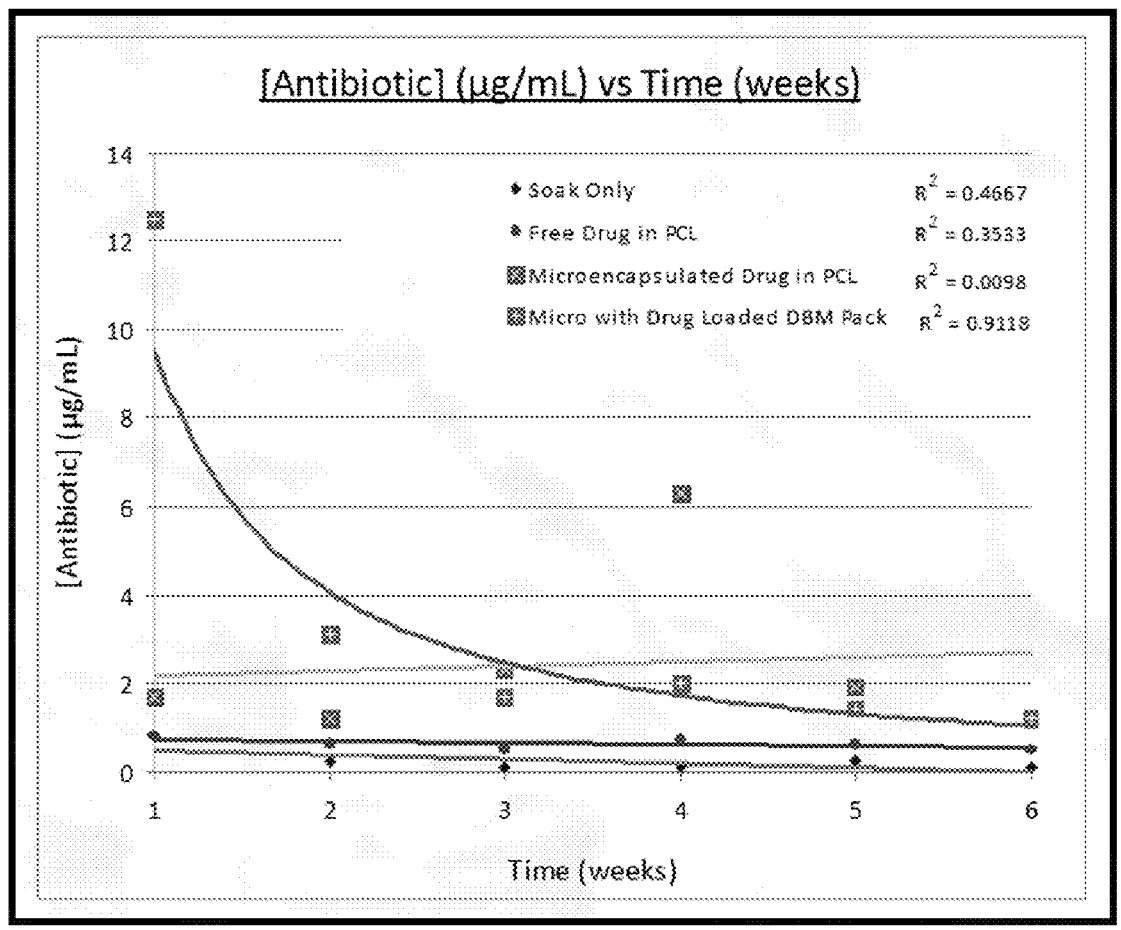
FIG. 3 depicts the adjusted timescale of FIG. 2 to highlight the polymer coating-mediated drug controlled release regime. The 1- to 6-week time course of drug release exhibits depletion of the 'drug soak only' biomaterial allograft samples (diffusive exhaustion without a polymer coated rate-controlling membrane) with longer-term maintenance of therapeutic levels of drug release only from the polymer-coated samples. Groups 1 through 3 are linear fit, while Group 4 is power fit to accommodate an extended bolus release from the DBM composite carrier, which greatly enhances the drug loading capacity and control of release of the substrate construct.
Figure 4:
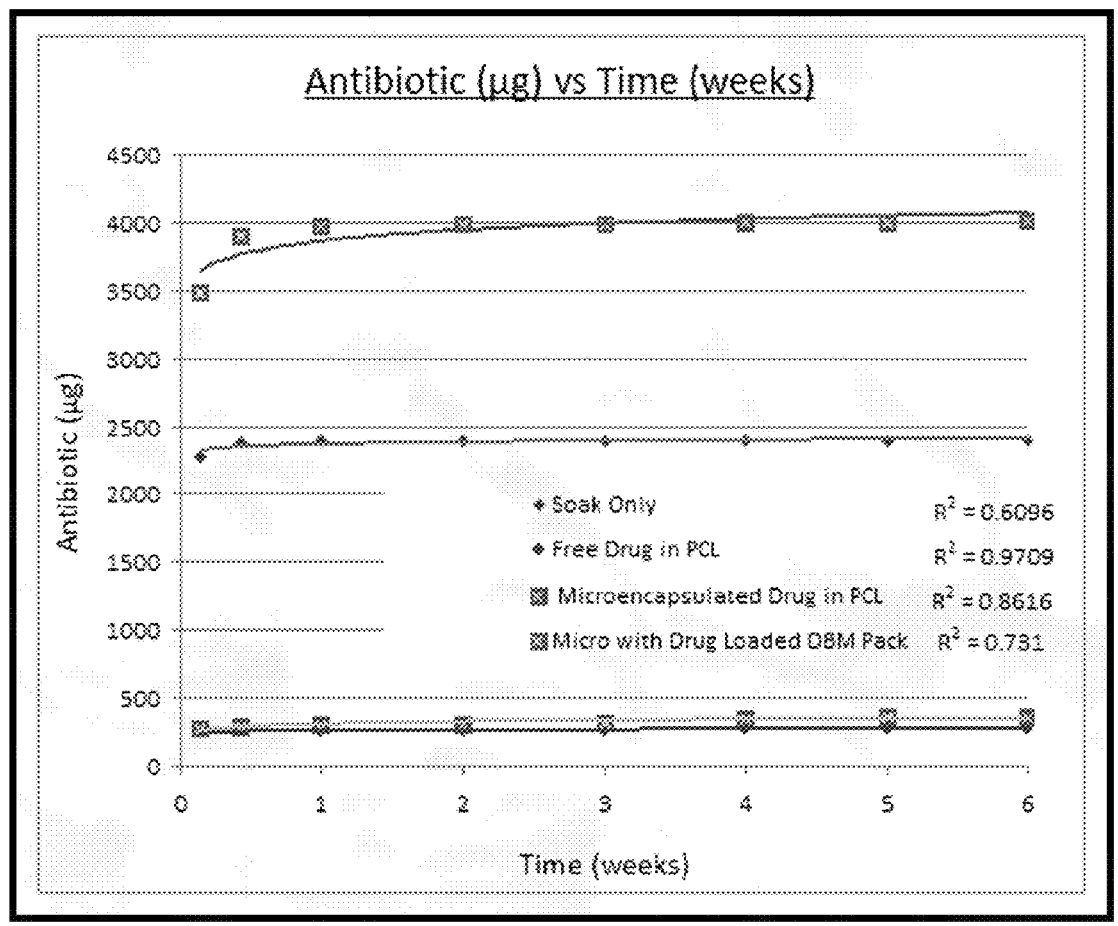
FIG. 4 shows cumulative (mass-based) drug release profiles over the 6-week time course, highlighting the differential loading attainable through different formulation methods. Direct allograft drug soaking and DBM-base allograft composite mixing provide variable, high drug loading. Using a rate-controlling membrane (i.e., degradable polymer coating) to modulate drug release yields extended dosing and controlled release while incorporating less total drug. All curves are logarithmic fit.
Figure 5:
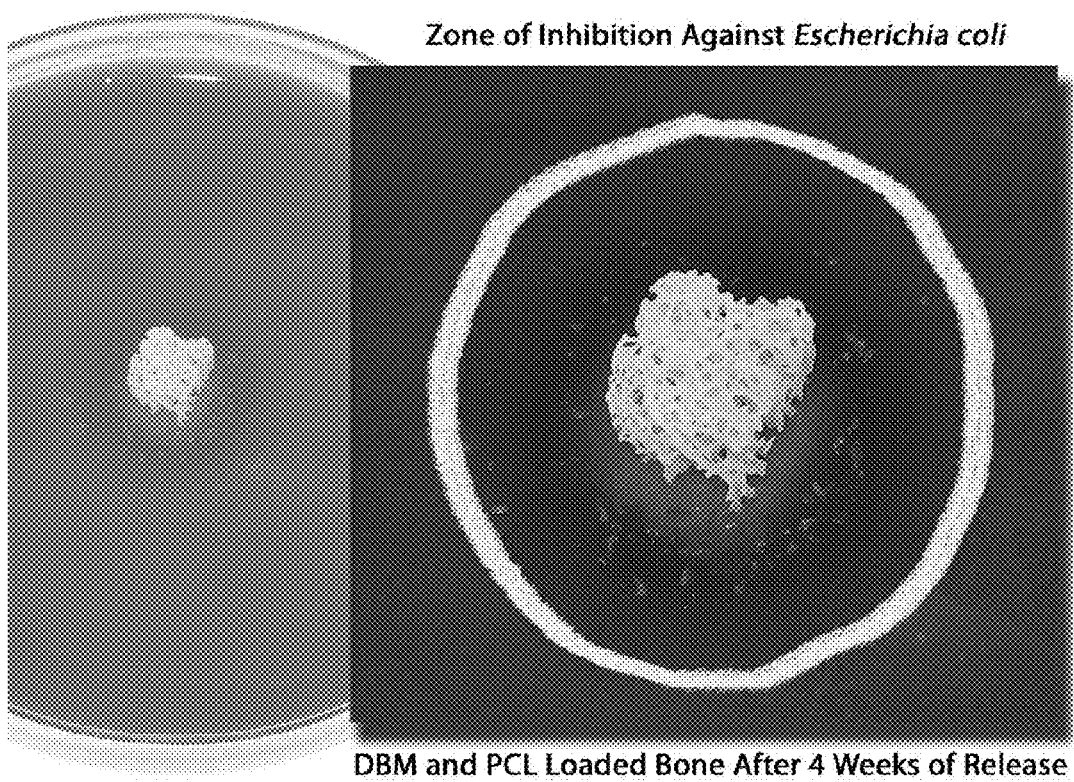
FIG. 5 displays the zone of inhibition (ZOI) against *Escherichia coli* cultures in agar plates as exhibited by an allograft morsel coated with gentamicin-impregnated 200,000 Da molecular weight PCL and packed with gentamicin-containing DBM infused throughout its pore structure, where the ZOI distance for the image is 7.49 mm and the bone allograft crouton surface area in contact with agar is 59.85 $mm^2$. The ZOI was measured as the distance from the edge of the bone crouton to the perimeter of the region in which no bacterial film could be visible discerned. Efficacious ZOI results indicate maintenance of therapeutic drug bioactivity throughout combination allograft fabrication and subsequent drug release.
Figure 6:
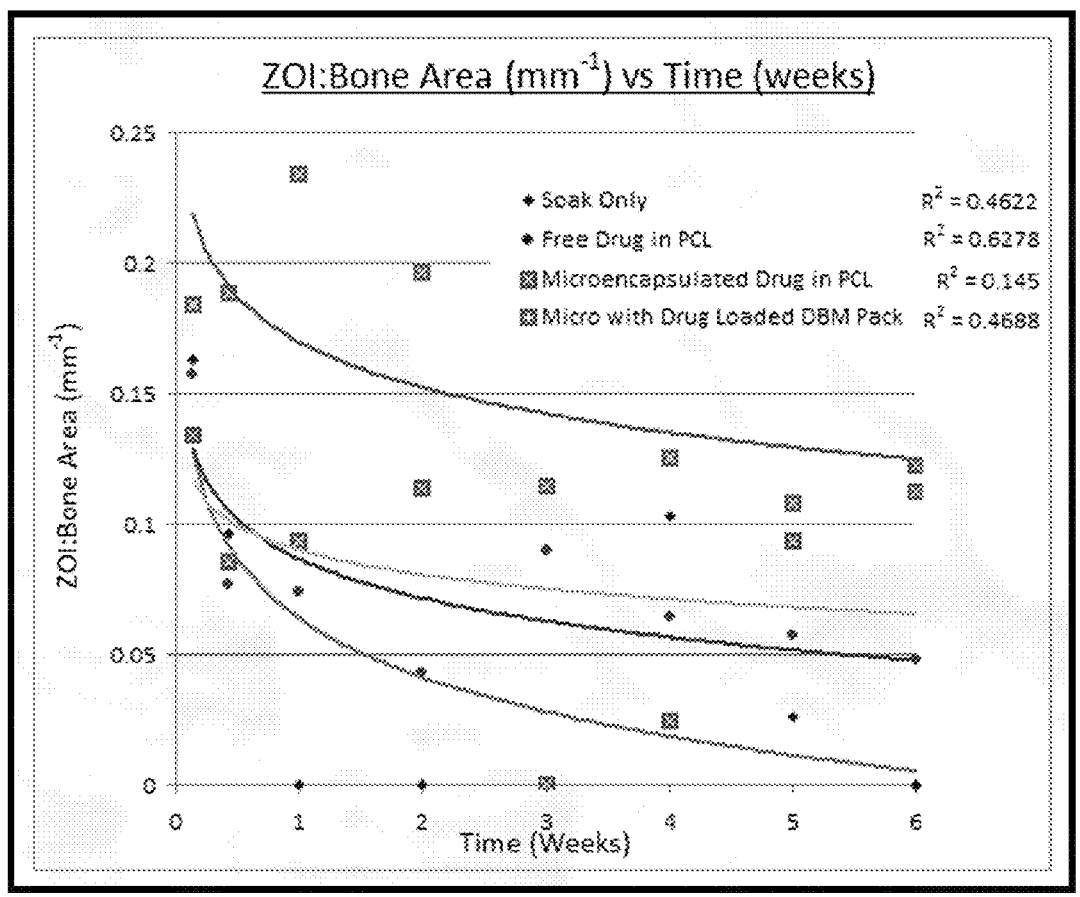
FIG. 6 is a graph plotting zones of inhibition in agar cultures as a function of the duration of drug release, generated by antibiotic eluted from allograft combination biomaterial constructs. "Drug soak-only" crouton samples produce no ZOI after 1 week of drug release. Controlling drug release with a PCL coating prolongs drug release and its resulting pharmacological efficacy throughout the assigned 6-week therapeutic window. Group 4 demonstrates the most potent bacterial killing capacity at all time points. Drug loading in a PCL matrix exhibits clear advantage over traditional "drug soak-only" approaches. All curves are logarithmic fit.
Figure 7:
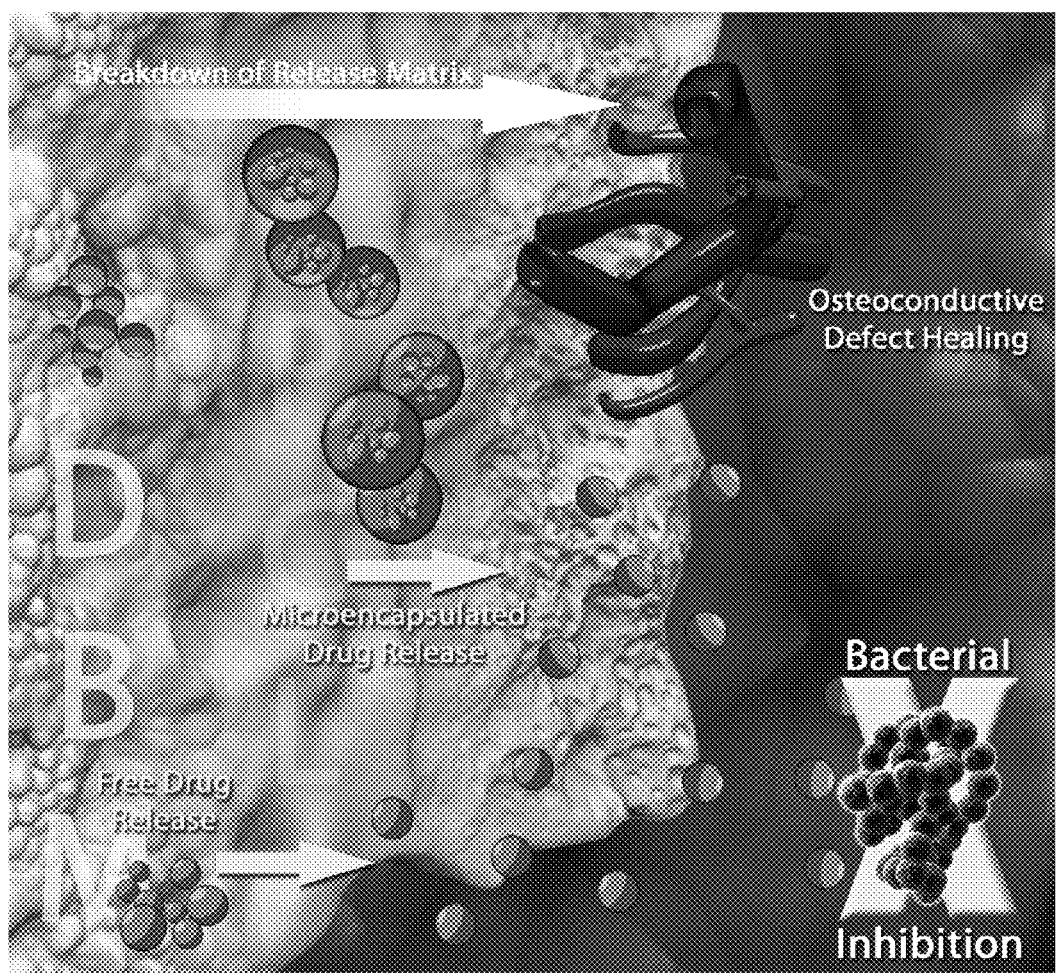
FIG. 7 is a graphical representation of the allograft drug loading and polymer coating degradation scheme, highlighting the flexibility in multiple bioactive or pharmaceutically active drug incorporation, and two primary end points of therapeutic enhancement: greatly minimizing the probability of infection (via antibiotics) and facilitated, potentially accelerated orthopaedic healing (via osteoconductive substrates and polymer-encapsulated osteoinductive growth factors). Additionally, FIG. 7 visualizes further the potential polymer matrix layering strategy proposed in FIG. 1.

The present invention discloses an antibiotic loading strategy for allograft bone grafts which fills bone defects in both clinical infections and surgical sites. The disclosed construct uses a layered degradable resorbable polycaprolactone synthetic polymer coating over an allograft bone crouton infused with demineralized bone matrix (DBM) (tier 4 release, FIG. 1). Microencapsulated gentamicin is incorporated into the degradable polymer coating to facilitate a controlled and extended local release of the antibiotic at the site of placement (FIG. 1). The experimental elution tests demonstrated not only an effective early bolus release, but also a sustained release over 6 weeks (FIGS. 2-4). The prolonged effect of this drug release will ensure that sufficient amounts of antibiotic are present to inhibit microbial growth and prevent recurrent pathologies, such as biofilms and development of antibiotic-resistant microbes around the release site. Furthermore, functional testing with bacterial inhibition studies also provided excellent bacterial suppression both at early and late time intervals (FIGS. 5-6). Ultimately, critical structural, space filling, osteoinductive, and conductive properties of the clinically accepted bone filler material were maintained with these new antimicrobial properties (FIG. 7).

The multi-level, tunable release of antibiotic from this combination biomaterial is a powerful anti-infective attribute of bone filler applications which is currently unavailable. The disclosed construct could be applied to a large number of foot and leg bone infections associated with diabetes, in addition to orthopedic and dental infections. Perhaps the greatest demand for an antibiotic-releasing bone filler would be in a sterile surgical site with associated bone loss, implant use, revision surgeries, critical bone defects, osteosarcoma resections, and trauma injury. Antibiotic delivering bone graft will provide local bactericidal drug concentrations to prevent infections not provided by prophylactic intravenous antibiotics or other bone grafting materials commonly used today.

2. Tobramycin Release Profiles from PCL Matrices a. Construction of Graft

Allograft cancellous croutons were cut to uniform size and weighed. Tobramycin powder was commercially microencapsulated utilizing lipid spray microspheres. PCL was dissolved at 60 mg/ml in 47 degrees centigrade acetone. Tobramycin powder and microencapsulated tobramycin were mixed with solvated PCL. Either free or microencapsulated tobramycin was mixed to the liquid PCL. 2 mg of antibiotic was used for each bone specimen. For uniform application, a pressurized fine spray was used to apply the PCL solution directly to the cancellous croutons as it rotated axially on a stationary ring stand. Air drying for 2 hours allowed the acetone to dissipate, creating a thin coating on the bone graft material.

b. Release Profiles

Release profile experiments were performed as follows: cancellous bone chips treated to the four prescribed regimens, [(1) 10,000 mol. wt. PCL, free tobramycin, (2) 10,000 mol. wt. PCL, microencapsulated tobramycin, (3) 80,000 mol. wt. PCL, free tobramycin, and (4) 80,000 mol. wt. PCL, microencapsulated tobramycin] were allowed to release drug into a 5 ml volume of simulated body fluid (SBF) for the eight assigned time points out to 6 weeks. Release fluid was replaced at every time point and samples saved for drug quantification analysis.

c. Results

Figure 8:
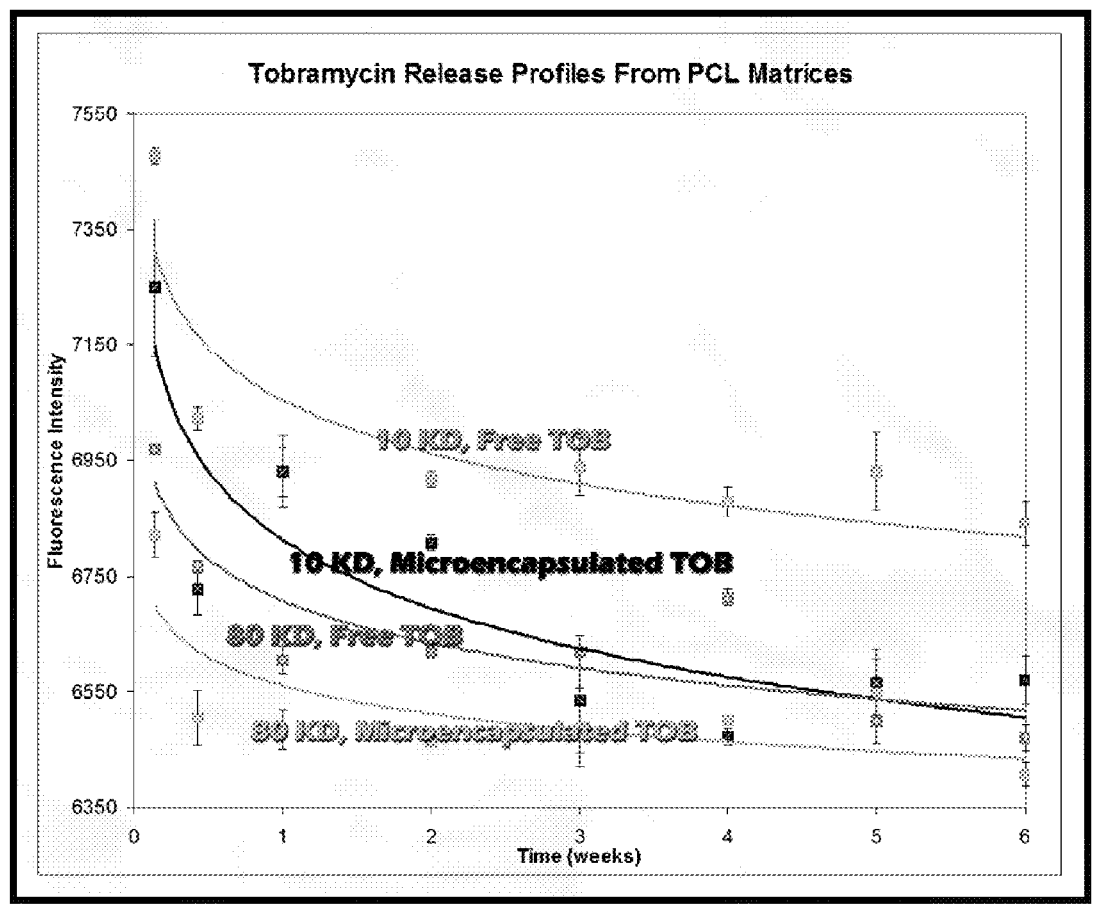
FIG. 8 is a graph of tobramycin release profiles from bone allograft preparations based off varying [1] PCL polymer coating molecular weight (10,000 Da versus 80,000 Da) and [2] state of drug microencapsulation within the polymer coating (encapsulated drug vs unencapsulated drug). The units given are relative fluorescence, correlating to a relative amount of tobramycin present as determined by the orthophthalaldehyde (OPA) quantification assay. Emphasis is placed on the relationship between the curves that demonstrate: [A] low molecular weight PCL coatings release more drug per unit time than their high molecular weight PCL coating analogs, and [B] drug loaded into the polymer coating in a microencapsulation form (as opposed to free drug) further slows drug release from the polymer coating but to an intermediate degree when compared to changes in polymer coating molecular weight. Collectively, these results indicate that a high degree of controlled drug delivery is both tunable, controlled and attainable in rate-controlled, extended release from the polymer coatings implementing this proposed 'tiered' system for drug loading and release from the tissue graft biomaterials.
Figure 9:
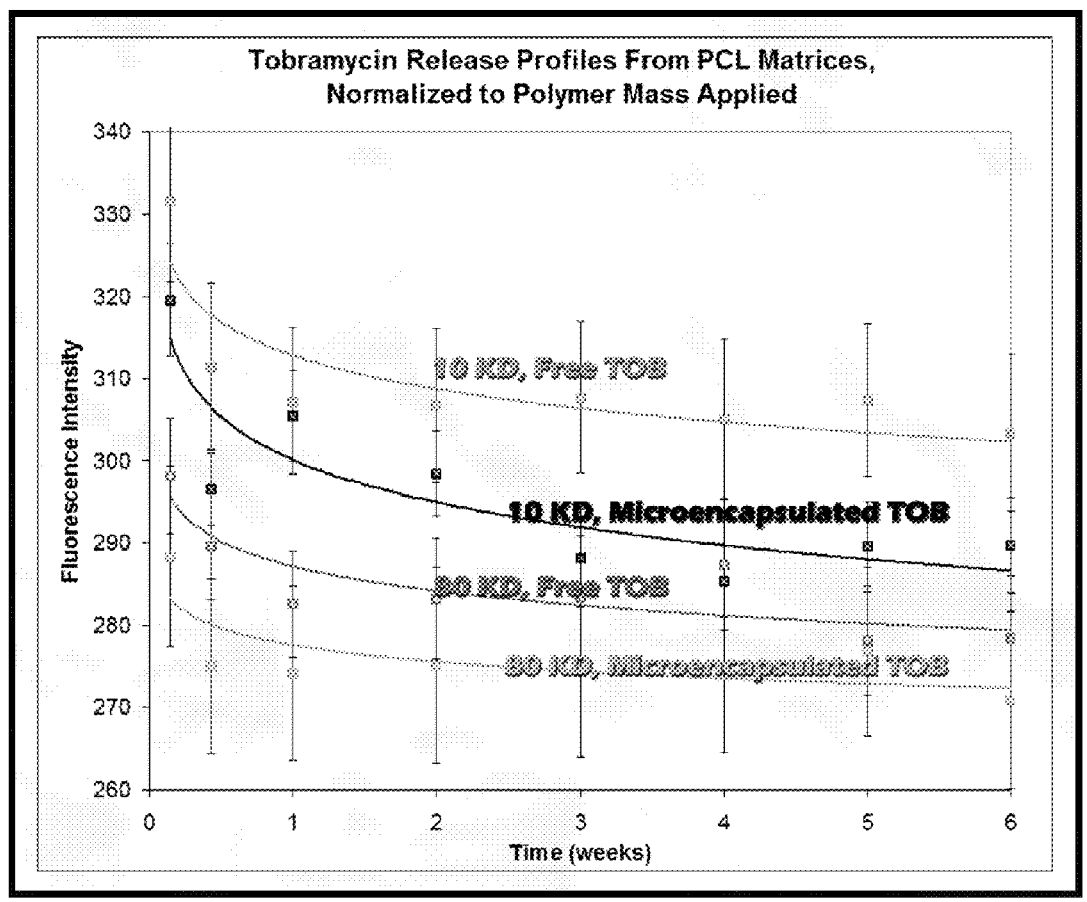
FIG. 9 is a plot of data found in FIG. 8 normalized to polymer coating mass applied to bone graft biomaterials. Due to variation inherent to bench-scale spray deposition methods and inherent to the allograft materials geometries and sizes, it is difficult to apply precisely the same amount of polymer coating to each bone morsel. Upon normalizing the release data, the same trends become clearly apparent as described in FIG. 8, namely modulation of polymer coating molecular weight and drug encapsulation state affect the amount of drug eluted per unit time in a predictable, tunable manner to provide controlled dosing and extended release.

Cancellous bone chips treated with lower molecular weight PCL coatings and tobramycin release more drug at each timepoint. Microencapsulation of tobramycin reduces the amount of drug release at each time point (FIG. 8). Since drug loading is equal among each sample, release profiles are solely a function of the polymer matrix properties and microencapsulated drug loading. In both cases, the molecular weights (10,000 mol. Wt. and 80,000 mol. wt.) exhibit strong controlled release kinetics (FIG. 8) and reach near zero-order kinetics after a week. Furthermore, each absorbance is normalized to the amount of polymer (and likewise the amount of drug) that is loaded on each sample (FIG. 9). Given the variable nature of allograft bone as a substrate, in addition to the inability to apply extremely accurate amounts of material with the spray fabrication method at benchtop scale, applied polymer coating weight is normalized to minimize intra-cohort variability. The rates of drug release exhaustion from the polymers are quite similar, but the amount delivered per unit time is a function of the polymer molecular weight. Given the same drug loadings between a high and low molecular weight matrix, the low molecular weight PCL allows more rapid drug release and earlier dose exhaustion; the higher molecular weight PCL produces longer extended drug release.

3. A Method of Using Controlled Release Tissue Graft Combination Biomaterials for Treatment of Osteonecrosis of the Femoral Head (Prophetic)

a. Construction of Graft

Osteoconductive materials, such as allograft cancellous croutons, are cut to uniform size and weighed. A bioactive agent, such as gentamicin powder, is microencapsulated utilizing lipid spray microspheres. Six grams of PCL are dissolved in 150 milliliters of acetone at 47 degrees centigrade. Gentamicin powder and microencapsulated gentamicin are mixed with polycaprolactone (PCL) solution. About 6.25 mg of antibiotic is used for each bone specimen. A pressurized fine spray is used to apply the PCL solution directly to the cancellous bone pieces for uniform application. Air drying for 2 hours allows the acetone to dissipate, creating a thin coat on the bone. DBM is loaded with 40 mg/ml of gentamicin and packed into the PCL-coated crouton as shown in FIG. 1.

b. Implantation of the Graft

The dead bone is removed with a high speed burr 10 or other instruments. The viable bone chips are taken out from the femoral head and neck portion with a chisel or gouge for later use. If the femoral head is collapsed, the collapsed portion is elevated with an elevator or other instruments. A window made in the femoral head is trimmed for the insertion of the cancellous croutons. The size of the cancellous crouton should be matched to the window for tight impaction of the cancellous crouton. The cancellous crouton is then inserted into the femoral head, and bone chips and other biological materials are impacted into empty spaces between the cartilage cap and the cancellous crouton. The joint capsule is not closed. The donor site of the iliac crest is then reconstructed with the insertion of bone or with further polymer-coated bone graft substitute biomaterials. They are tied with a suture to the host bone in order not to be dislodged. The muscle fascia and subcutaneous tissue are repaired over a suction drain, and the skin is then closed.

c. Results

The biological agent is released from the cancellous crouton over a period of 6 weeks, or any therapeutically recommended time period. The patients is monitored postoperatively and shows no signs of infection over a period of 6 weeks, or as recommended by the surgeon.

4. A Method of Using Controlled Release Tissue Graft Combination Biomaterials to Treat Injury to the Mandible (Prophetic)

a. Construction of Graft

Osteoconductive materials, such as allograft cancellous croutons, are cut to uniform size and weighed. A bioactive agent, such as gentamicin powder, is microencapsulated utilizing lipid spray microspheres. Six grams of PCL are dissolved in 150 milliliters of acetone at 47 degrees centigrade. Gentamicin powder and microencapsulated gentamicin are mixed with polycaprolactone (PCL) solution. About 6.25 mg of antibiotic is used for each bone specimen. A pressurized fine spray is used to apply the PCL solution directly to the cancellous croutons or particles for uniform application. Air drying for 2 hours allows the acetone to dissipate, creating a thin coat on the bone. DBM is loaded with 40 mg/ml of gentamicin and packed into the PCL coated crouton as shown in FIG. 1.

b. Implantation of the Graft

The patient's injury site is prepped routinely as per surgery. The maxillo-mandibular occlusion is maintained by inter-maxillary wire fixation to maintain jaw relations. The appropriate length of the transport segment should be estimated before surgery and a number of plates with different lengths should be available during surgery to choose from. The device can be fixed to the mandibular bone stumps either before or after removal of the tumor segment by three bicortical screws on each side as in traditional reconstruction plate, leaving out approximately 2 cm of bone at the edge of one of the two bone segments, classically the posterior segment, so that it can be separated and fixed to the transport unit. After tumor resection, the transport unit is fixed to the potential transport block (transport disc) through the two miniplates either before or after its separation.

The size of the cancellous crouton should be matched to the window for tight impaction of the cancellous crouton. The cancellous crouton is then inserted into the window, and polymer-coated drug releasing allograft graft particles, chips, autologous bone chips and other biological materials are impacted into empty spaces. The surgical site is secured and closed.

c. Results

The bioactive or pharmaceutical agent(s) will be released from the polymer-coated combination allograft biomaterial cancellous crouton over a period of 6 weeks, or any therapeutically recommended time period. The patients will be monitored postoperatively for signs of infection during hospital stay over a period of 6 weeks postoperatively, or as recommended by the surgeon.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A bone graft combination biomaterial comprising:
   a. a biocompatible, osteoconductive, porous substrate, wherein the substrate comprises a material selected from the group consisting of an allograft bone and an alloplastic material, wherein the substrate is devoid of collagen and wherein the substrate comprises in its pores demineralized bone matrix and a first antimicrobial agent; and
   b. a film coating on the substrate surface, the coating comprising a degradable rate controlling polymer, wherein said polymer is polycaprolactone having a molecular weight from about 10 kD to about 200 kD, admixed with at least one second antimicrobial agent microencapsulated in microspheres or nanoencapsulated in nanospheres, wherein the first antimicrobial agent and the second antimicrobial agent can be the same or different, and wherein the polycaprolactone has a structure and a molecular weight selected to degrade over a time period of about six weeks when implanted within a subject and thereby release the agent over the time period.

2. The combination biomaterial of claim 1, wherein the substrate further comprises bone powder.

3. The combination biomaterial of claim 1, wherein the polycaprolactone has a molecular weight from about 10 kD to about 100 kD.

4. The combination biomaterial of claim 1, wherein the alloplastic material is (tri)calcium phosphate.

5. The combination biomaterial of claim 1, wherein the alloplastic material is hydroxyapatite.

6. The combination biomaterial of claim 1, wherein the alloplastic material is calcium sulfate.

7. The combination biomaterial of claim 1, wherein the alloplastic material is calcium phosphate.

* * * * *